United States Patent
Ishibashi et al.

(10) Patent No.: US 11,352,312 B2
(45) Date of Patent: Jun. 7, 2022

(54) DIESTER COMPOUND HAVING A DIMETHYLCYCLOBUTANE RING, A PROCESS FOR PREPARING THE SAME, AND A PROCESS FOR PREPARING DIMETHYLCYCLOBUTANE COMPOUND DERIVED FROM THE DIESTER COMPOUND

(71) Applicant: Shin-Etsu Chemical Co., Ltd., Tokyo (JP)

(72) Inventors: Naoki Ishibashi, Niigata (JP); Yusuke Nagae, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/930,578

(22) Filed: Jul. 16, 2020

(65) Prior Publication Data

US 2021/0017115 A1 Jan. 21, 2021

(30) Foreign Application Priority Data

Jul. 17, 2019 (JP) .............. JP2019-132129
Apr. 2, 2020 (JP) .............. JP2020-067072

(51) Int. Cl.
| | |
|---|---|
| C07C 67/42 | (2006.01) |
| C07C 67/10 | (2006.01) |
| C07C 67/14 | (2006.01) |
| C07C 67/40 | (2006.01) |
| C07C 69/74 | (2006.01) |
| C07C 17/013 | (2006.01) |
| C07C 29/147 | (2006.01) |
| C07C 29/62 | (2006.01) |

(52) U.S. Cl.
CPC .......... *C07C 67/42* (2013.01); *C07C 17/013* (2013.01); *C07C 29/147* (2013.01); *C07C 29/62* (2013.01); *C07C 67/10* (2013.01); *C07C 67/14* (2013.01); *C07C 67/40* (2013.01); *C07C 69/74* (2013.01); C07C 2601/04 (2017.05)

(58) Field of Classification Search
CPC ....... C07C 69/74; C07C 29/147; C07C 29/14; C07C 29/10; C07C 29/40; C07C 29/42
USPC ....................................................... 560/123
See application file for complete search history.

(56) References Cited

FOREIGN PATENT DOCUMENTS

| | | | |
|---|---|---|---|
| DE | 2539048 A1 | | 3/1976 |
| EP | 0051791 A1 | | 5/1982 |
| GB | 1524682 A | | 9/1978 |
| WO | WO 2015125785 | * | 8/2015 |

OTHER PUBLICATIONS

Arai et al. "Identification of a Sex Pheromone Component of Pseudococcus cryptus4" Journal of Chemical Ecology, 29(10):2213-2223 (2003).
Bierl-Leonhardt et al. "Isolation, Identification and Synthesis of the Sex Pheromone of the Citrus Mealybug, Planococcus Citri (Risso)" Tetrahedron Letters, 22(5):389-392 (1981).
Kawano et al. "Formal [4+2] cycloaddition of cyclobutanones bearing alkyne-cobalt complex at their 3-positions" Tetrahedron Letters, 53(4):432-434 (2012).
Millar et al. "Identification of the Sex Pheromone of the Invasive Scale Acutaspis albopicta (Hemiptera: Diaspididae), Arriving in California on Shipments of Avocados From Mexico" Journal of Economic Entomology, 105(2):497-504 (2012).
Passaro et al. "Synthesis of the Female Sex Pheromone of the Citrus Mealybug. Planococcus citri" Journal of Agricultural and Food Chemistry, 52(10):2896-2899 (2004).
Tabata et al. "Sex Pheromone of the Cotton Mealybug, Phenacoccus solenopsis, with an Unusual Cyclobutane Structure" Journal of Chemical Ecology, 42(11):1193-1200 (2016).
Zhang et al. "Chiral synthesis of maconelliol: a novel cyclobutanoid terpene alcohol from pink hibiscus mealybug, Maconellicoccus hirsutus" Tetrahedron Letters, 45(51):9401-9403 (2004).
Zhang et al. "Sex pheromone of the pink hibiscus mealybug, Maconellicoccus hirsutus, contains an unusual cyclobutanoid monoterpene" PNAS, 101(26):9601-9606 (2004).

(Continued)

*Primary Examiner* — Ana Z Muresan
(74) *Attorney, Agent, or Firm* — Myers Bigel, P.A.

(57) ABSTRACT

The present invention provides a process for preparing a diester compound of the following general formula (1), having a dimethylcyclobutane ring, wherein $R^1$ and $R^2$ represent, independently of each other, a monovalent hydrocarbon group having 1 to 10 carbon atoms, the process comprising reacting a dimethylcyclobutanone compound of the following general formula (2), wherein $R^1$ is as defined above, with a phosphonic ester compound of the following general formula (3), wherein $R^2$ and $R^3$ represent, independently of each other, a monovalent hydrocarbon group having 1 to 10 carbon atoms, to produce the diester compound (1), having a dimethylcyclobutane ring.

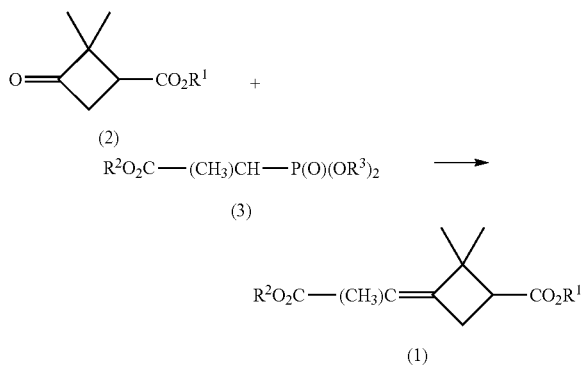

4 Claims, No Drawings

(56) References Cited

OTHER PUBLICATIONS

Extended European Search Report corresponding to European Patent Application No. 20185855.2 (6 pages) (dated Nov. 30, 2020).
Extended European Search Report corresponding to European Patent Application No. 20185859.4 (8 pages) (dated Nov. 30, 2020).

* cited by examiner

DIESTER COMPOUND HAVING A DIMETHYLCYCLOBUTANE RING, A PROCESS FOR PREPARING THE SAME, AND A PROCESS FOR PREPARING DIMETHYLCYCLOBUTANE COMPOUND DERIVED FROM THE DIESTER COMPOUND

TECHNICAL FIELD

The present invention relates to a diester compound having a dimethylcyclobutane ring which is a useful intermediate for synthesis of insect sex pheromones, and a process for preparing the diester compound. The present invention relates also to a process for preparing a dimethylcyclobutane compound derived from the diester compound having a dimethylcyclobutane ring.

BACKGROUND ART

Insect sex pheromones are biologically active substances which usually have a function of attracting male individuals to female individuals, and exhibit high attracting activities in small amounts. Sex pheromones are widely used as a means of forecasting outbreaks of pests and confirming geographic spread (invasion into a specific area), and as a means of controlling pests. Widely used methods am a mass trapping method, a lure & kill or attract & kill method, a lure & infect or attract & infect method, and a mating disruption method. Before practical use of sex pheromones, economical production of a sufficient amount of a pheromone substance is required for basic research and also for applications.

An example of a unique structure among the chemical structures for the sex pheromones is a cyclobutane structure. For instance, the sex pheromone of *Planococcus citri* (generic name: Citrus mealybug) which is an economically serious pest and spread widely throughout the world to infest citrus is (+)-cis-(3-isopropenyl-2,2-dimethylcyclobutyl) methyl acetate, as reported by Bierl-Leonhardt et al. (Non-Patent Literature 1, as listed below). The sex pheromones of *Pseudococcus cryptyptus* (generic name: Citriculus mealybug) and *Acutaspis albopicta* (generic name: Albopicta scale) also have a structure of cis-(3-isopropenyl-2,2-dimethylcyclobutyl)methyl ester of a carboxylic acid, similar to the sex pheromone of Citrus mearybug (Non-Patent Literatures 2 and 3, as listed below). Further, species such as *Maconellicoccus hirstus* (generic name: Pink hibiscus mealybug) and *Phenacoccus solenopsis* (generic name: Cotton mealybug) are also known, the sex pheromon of which is (3-isopropylidene-2,2-dimethylcyclobutyl)methyl ester, in which a position of a double bond is different from that of the sex pheromone of Citrus mealybug (Non-Patent Literatures 4 and 5, as listed below).

In typical methods for preparing sex pheromones having these cyclobutane structures, pinene is used as a starting material. For instance, the following method is reported by Passaro et al.; pinene was oxidized to produce verbenol or verbenone, which are further oxidized to cleave the double bond, followed by methylation of the ketone group, reduction of the carboxylic group and acetylation to obtain the sex pheromone of Citrus mealybug (Non-Patent Literature 6, as listed below). The following method is reported by Zhang et al.; verbenone is oxidized, followed by methylation of a the ketone, lactonization and cleavage of the lactone ring to construct an isopropylidene group, and reduction of the carboxylic group to produce (3-isopropylidene-2,2-dimethylcyclobutyl)methanol which corresponds to the alcohol moiety in the sex pheromone of Pink hibiscus mealybug and Cotton mealybug (Non-Patent Literature 7, as listed below).

LIST OF THE PRIOR ART

Non-Patent Literatures

[Non-Patent Literature 1] Tetrahedron. Lett. 22, 389 (1981)
[Non-Patent Literature 2] J. Chem. Ecol. 29, 2213 (2003)
[Non-Patent Literature 3] J. Econ. Entomol. 105, 497 (2012)
[Non-Patent Literature 4] Proc. Nal. Acad. Sci. 101, 9601 (2004)
[Non-Patent Literature 5] J. Chem. Ecol. 42, 1193 (2016)
[Non-Patent Literature 6] J. Agric. Food Chem. 2004, 52, 2896 (2004)
[Non-Patent Literature 7] Tetrahedron. Lett. 45, 9401 (2004)

SUMMARY OF THE INVENTION

However, lead tetracetate or chromium oxide is used for the oxidation of pinene into verbenol or verbenone in the method described in Non-Patent Literature 6, leaving a large amount of heavy metal waste which is harmful and gives high environmental burden. Further, these oxidizing agents may cause explosion and are not industrially practical. An expensive ruthenium catalyst is used to further oxidize verbenol or verbenone, and, therefore, industrial practice is difficult in view of the economy. The oxidation of pinene into verbenone is carried out in an oxygen atmosphere in the production method described in Non-Patent Literature 7. This is difficult to be industrially practiced in view of the safety and requires a reaction time of so many days of 7, which is inefficient and uneconomical. Further, an expensive ruthenium catalyst is used for the oxidation of verbenone, which isABA uneconomical, as in Non-Patent Literature 6.

An efficient and industrially practical production method capable of supplying a sufficient amount of the pheromone substances is eagerly wanted for basic biological and agricultural research on sex pheromone compounds having a cyclobutane structure, like the sex pheromone of Citrus mealybug and further for the purpose of application and practical use.

The present invention has been made in these circumstances, and aims it to provide an efficient and industrially practical method for producing a dimethylcyclobutane compound which is useful as a synthetic intermediate for sex pheromone compounds having a cyclobutane structure, and to provide the compound.

As a result of the intensive researches in order to solve the problems above, the present inventors have found a process for efficiently and industrially practically preparing sex pheromones having a cyclobutane structure, using a diester compound of the following general formula (1), having a dimethylcyclobutane ring, without an oxidation reaction which is difficult to carry out industrially in view of the safety, the economy and the environmental burden, and thus have completed the present invention.

According to one aspect of the present invention, there is provided a process for preparing a diester compound of the following general formula (1), having a dimethylcyclobutane ring,

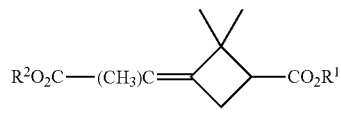

(1)

wherein $R^1$ and $R^2$ represent, independently of each other, a monovalent hydrocarbon group having 1 to 10 carbon atoms, the process comprising reacting a dimethylcyclobutanone compound of the following general formula (2):

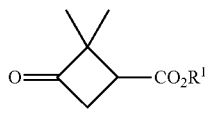
(2)

wherein $R^1$ is as defined above,
with a phosphonic ester compound of the following general formula (3):

$$R^2O_2C\text{---}(CH_3)CH\text{---}P(O)(OR^3)_2 \quad (3)$$

wherein $R^2$ is as defined above, and $R^3$ represents a monovalent hydrocarbon group having 1 to 10 carbon atoms, especially in an olefination reaction, preferably a Homer Wadsworth-Emmons reaction, to produce the diester compound (1), having a dimethylcyclobutane ring.

According to another aspect of the present invention, there is provided a process for a diol compound of the following formula (4), having a dimethylcyclobutane ring,

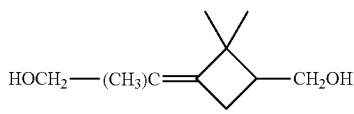
(4)

the process comprising subjecting a diester compound of the following general formula (1), having a dimethylcyclobutane ring,

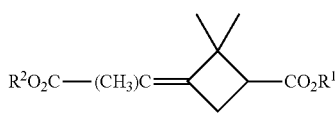
(1)

wherein $R^1$ and $R^2$ represent, independently of each other, a monovalent hydrocarbon group having 1 to 10 carbon atoms,
to a reduction reaction to produce the diol compound (4), having a dimethylcyclobutane ring.

According to another aspect of the present invention, there is provided a process for a dimethylcyclobutane compound of the following general formula (5):

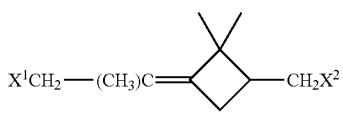
(5)

wherein $X^1$ represents an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms or a halogen atom; and $X^2$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms or a halogen atom, the process comprising the step of the aforesaid process for preparing the diol compound (4), having a dimethylcyclobutane ring; and changing a hydroxyl group in the moiety of $HOCH_2\text{---}(CH_3)C=$, and optionally a hydroxyl group in the moiety of $\text{---}CH_2OH$, in the diol compound (4), having a dimethylcyclobutane ring, to $X^1$ and $X^2$, respectively to produce the dimethylcyclobutane compound (5).

According to another aspect of the present invention, there is provided a process for preparing an isopropenyl dimethylcyclobutane compound of the following formula (6):

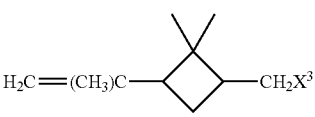
(6)

wherein $X^3$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, or a halogen atom, and/or an isopropylidene dimethylcyclobutane compound of the following formula (7):

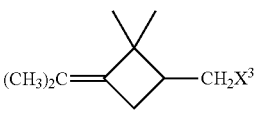
(7)

wherein $X^3$ is as defined above;
the process comprising
the aforesaid process for preparing the dimethylcyclobutane compound (5); and
subjecting the dimethylcyclobutane compound (5) to a reduction reaction to produce the isopropenyl dimethylcyclobutane compound (6) and/or the isopropylidene dimethylcyclobutane compound (7).

According to another aspect of the present invention, there is provided a process for preparing an isopropenyl dimethylcyclobutane compound (6') and/or an isopropylidene dimethylcyclobutane compound (7'), the process comprising
the aforesaid process for preparing the isopropenyl dimethylcyclobutane compound (6) and/or the isopropylidene dimethylcyclobutane compound (7); and
changing a specific group, $X^3$, in the isopropenyl dimethylcyclobutane compound (6) and/or the isopropylidene dimethylcyclobutane compound (7) to another group, $X^3$, among the options for $X^3$ defined above to produce the isopropenyl dimethylcyclobutane compound (6') and/or the isopropylidene dimethylcyclobutane compound (7').

According to another aspect of the present invention, there is provided a diester compound of the following general formula (1), having a dimethylcyclobutane ring,

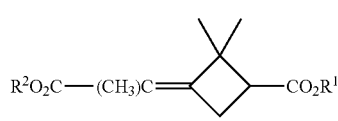

(1)

wherein $R^1$ and $R^2$ represent, independently of each other, a monovalent hydrocarbon group having 1 to 10 carbon atoms.

According to the present invention, a sex pheromone compound having a cyclobutane structure can be prepared efficiently and industrially without an oxidation reaction which are difficult to carry out industrially in view of safety, economy and environmental burden. The present invention is applicable to the preparation of cis-(3-isopropenyl-2,2-dimethylcyclobutyl)methy ester which is the sex pheromone of Citrus mealybug, Citriculus mealybug and Albopicta scale, and (3-isopropylidene-2,2-dimethylcyclobutyl)methyl ester which is the sex pheromone of Pink hibiscus mealybug and Cotton mealybug.

DETAILED DESCRIPTION OF THE INVENTION

In the chemical formulae of the intermediates, the reagents and the target compounds in the present specification, there may be some isomers having different substitution positions on the structure, or stereoisomers such as enantiomers or diastereoisomers. Unless otherwise stated, in each case, each chemical formula shall be interpreted to represent all of these isomers. Further, these isomers may be an isomer or a combination thereof.

[I] Diester Compound (1), Having a Dimethylcyclobutane Ring

First, the diester compound (1), having a dimethylcyclobutane ring, will be explained. The diester compound (1), having a dimethylcyclobutane ring, is represented by the following formula.

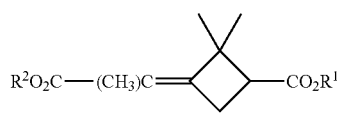

(1)

$R^1$ and $R^2$ represent, independently of each other, a monovalent hydrocarbon group having 1 to 10 carbon atoms. The number of carbon atoms of $R^1$ and $R^2$ is 1 to 10, preferably 1 to 5.

Examples of a monovalent hydrocarbon group include linear saturated hydrocarbon groups such as a methyl (Me) group, an ethyl (Et) group, an n-propyl (Pr) group, an n-butyl (Bu) group, an n-pentyl (Pen) group, an n-hexyl (Hex) group, an n-heptyl (Hep) group, an n-octyl (Oct) group, an n-nonyl (Non) group, and an n-decyl (Dec) group; branched saturated hydrocarbon groups such as an isopropyl (i-Pr) group, a sec-butyl group, an isobutyl (i-Bu) group, and a t-butyl (t-Bu) group; linear unsaturated hydrocarbon groups such as a 2-propenyl group and a 2-propynyl group; branched unsaturated hydrocarbon groups such as 2-methyl-2-propenyl group; cyclic hydrocarbon groups such as a cyclopropyl group, a 2-methylcyclopropyl group, a cyclobutyl group, a cyclopentyl group, and a cyclohexyl (c-Hex) group; and aromatic hydrocarbon groups such as a phenyl (Ph) group, a 2-methylphenyl group, and a 4-methylphenyl group; and further may include hydrocarbon groups having isomeric relation with the groups mentioned above.

A part of hydrogen atoms in these monovalent hydrocarbon groups may be substituted with a methyl group, an ethyl group, or a halogen atom. Examples of a halogen atom include a chlorine atom, a bromine atom, and an iodine atom.

Considering the reactivity in the reduction reaction as will be described hereinafter and/or the ease of purification after the reaction, monovalent hydrocarbon groups having 1 to 4 carbon atoms are preferred which have higher reactivity and whose by-produced alcohol can be easily removed by washing and concentration. Particularly preferred examples of $R^1$ and $R^2$ include a methyl group, an ethyl group, an n-propyl group, an isopropyl group, an n-butyl group, a sec-butyl group, an isobutyl group, and a t-butyl group, particularly a methyl group, an ethyl group, and an n-propyl group.

Examples of the diester compound (1), having a dimethylcyclobutane ring, include (S,Z)-3-(1-alkoxycarbonylethylidene)-2,2-dimethylcyclobutanecarboxylic acid ester compound of the following formula (1-1), (R,Z)-3-(1-alkoxycarbonylethylidene)-2,2-dimethylcyclobutanecarboxylic acid ester compound of the following formula (1-2), (S,E)-3-(1-alkoxycarbonylethylidene)-2,2-dimethylcyclobutanecarboxylic acid ester compound of the following formula (1-3), and (R,E)-3-(1-alkoxycarbonylethylidene)-2,2-dimethylcyclobutanecarboxylic acid ester compound of the following formula (1-4), and the racemates, diastereomeric mixtures and scalemic mixtures thereof.

(1-1)

(1-2)

(1-3)

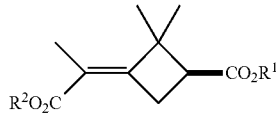

(1-4)

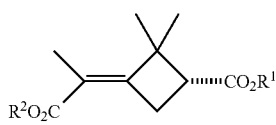

Particularly, examples of the diester compound (1), having a dimethylcyclobutane ring, include ethyl 3-(1-ethoxycarbonylethylidene)-2,2-dimethylcyclobutanecarboxylate (see Example 1) and the following diester compounds having a dimethylcyclobutane ring.

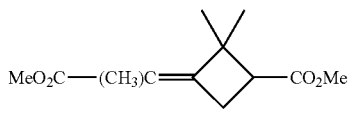

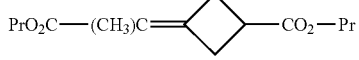

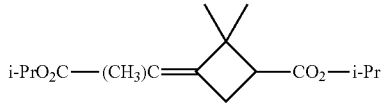

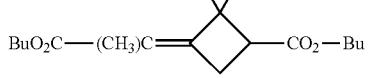

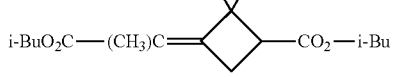

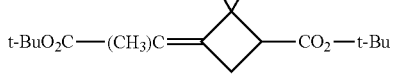

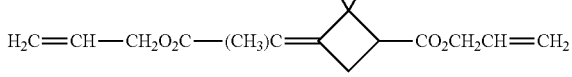

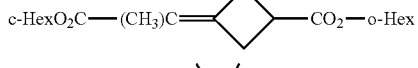

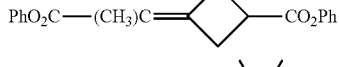

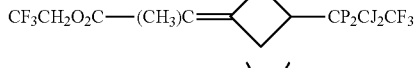

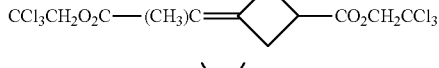

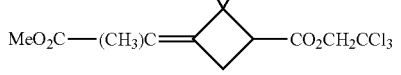

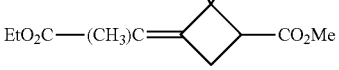

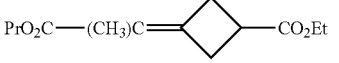

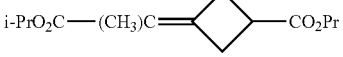

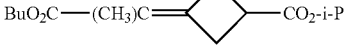

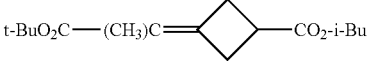

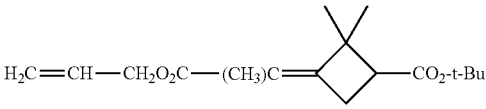

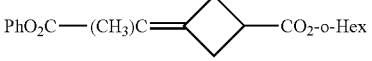

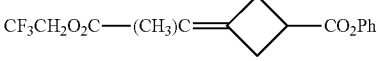

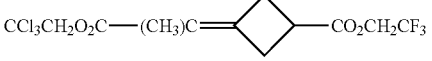

[II] Process for Preparing the Diester Compound (1), Having a Dimethylcyclobutane Ring Next, a process according to the following chemical reaction formula for preparing the diester compound (1), having a dimethylcyclobutane ring, will be explained hereinafter. The method comprises reacting a dimethylcyclobutanone compound of the following general formula (2) with a phosphonic ester compound of the following general formula (3), especially in an olefination reaction, preferably a Homer Wadsworth-Emmons reaction, to produce the diester compound (1), having a dimethylcyclobutane ring.

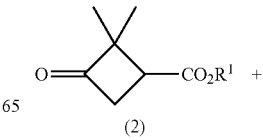

(2)

-continued

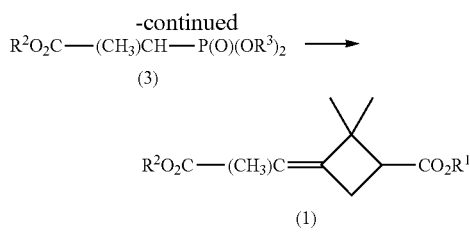

R¹ in the dimethylcyclobutanone compound (2) is as defined above.

Examples of the dimethylcyclobutanone compound (2) include (S)-3-oxo-2,2-dimethylyclobutancarboxylic acid ester compound of the following general formula (2-1), and (R)-3-oxo-2,2-dimethylcyclobutanecarboxylic acid ester compound (2-2), and the racemates and the scalemic mixtures thereof.

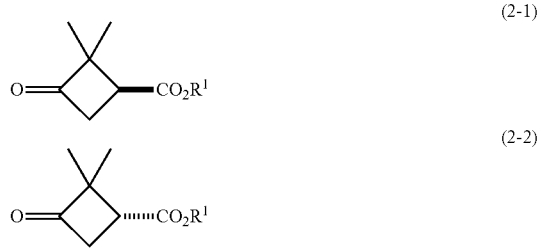

Examples of the dimethylcyclobutanone compound (2) include ethyl 2,2-dimethyl-3-oxocyclobutanecarboxylate (see Example 1 below). The dimethylcyclobutanone compound (2) may be used alone or in combination thereof. The dimethylcyclobutanone compound (2) may be commercially available one or may be synthesized in house.

R² in the phosphonic cater compound (3) is as defined above.

R³ in the phosphonic ester compound (3) represents a monovalent hydrocarbon group having 1 to 10 carbon atoms. The number of carbon atoms is 1 to 10, preferably 1 to 5.

Examples of a monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, and an n-decyl group; branched saturated hydrocarbon groups such as an isopropyl group, a sec-butyl group, an isobutyl group, a t-butyl group; linear unsaturated hydrocarbon groups such as a 2-propenyl group, and a 2-propynyl group; branched unsaturated hydrocarbon groups such as 2-methyl-2-propenyl group; cyclic hydrocarbon groups such as a cyclopropyl group, a 2-methylcyclopropyl group, a cyclobutyl group, a cyclopentyl group, and a cyclohexyl group; and aromatic hydrocarbon groups such as a phenyl group, a 2-methylphenyl group, and a 4-methylphenyl group; and further may include hydrocarbon groups having isomeric relation with the groups above.

A part of the hydrogen atoms of these monovalent hydrocarbon groups may be substituted with a methyl group, an ethyl group or a halogen atom. Examples of a halogen atom include a chlorine atom, a bromine atom, and an iodine atom.

Particularly preferred Examples of R³ include a methyl group, an ethyl group, an n-propyl group, an isopropyl group, an n-butyl group, and a phenyl group in view of the availability of the phosphonic ester compound (3).

Particularly, an example of the phosphonic ester compound (3) is triethyl 2-phosphonopropionate.

The phosphonic ester compound (3) may be used alone or in combination thereof. The phosphonic ester compound (3) may be commercially available one or may be synthesized in house.

An amount of the phosphonic ester compound (3) used is preferably from 0.7 to 5.0 mol, more preferably from 0.8 to 4.0 mol, and even more preferably from 0.9 to 3.0 mol, per mol of the dimethylcyclobutanone compound (2).

Examples of a base used in the aforesaid reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic basic compounds such as triethylamine, diisopropylethyamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 5.0 mol, more preferably from 0.8 to 4.0 mol, and even more preferably from 0.9 to 3.0 mol, per mot of the phosphonic ester compound (3).

The aforesaid reaction may be carried out in the presence of a Lewis acid.

Examples of a Lewis acid include lithium halides such as lithium chloride, lithium bromide, and lithium iodide.

The Lewis acid may be used alone or in combination thereof. The Lewis acid may be commercially available one.

An amount of the Lewis acid used is preferably from 0.7 to 5.0 mat, more preferably from 0.8 to 4.0 mol, and even more preferably from 0.9 to 3.0 mol, per mol of the phosphonic ester compound (3).

Examples of a solvent used in the reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitrites such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the dimethylcyclobutanone compound (2).

A reaction temperature in the aforesaid reaction is preferably from −78 to 180° C., more preferably from −60 to 160° C., and even more preferably from −40 to 140° C.

A reaction time in the aforesaid reaction may be set arbitrarily. It is desirable in view of the yield to monitor the reaction with gas chromatography (GC) or silica gel thin layer chromatography (TLC) to confirm completion of the reaction. A reaction time is usually about 0.5 to 24 hours.

[III] Process for Preparing the Diol Compound (4), Having a Dimethylcyclobutane Ring Next, a process for preparing the diol compound (4), having a dimethylcyclobutane ring according to the monitoring chemical reaction formula will be explained hereinafter. The method comprises subjecting the diester compound (1), having a dimethylcyclobutane ring, to a reduction reaction to produce the diol compound (4), having a dimethylcyclobutane ring (see Example 2 below).

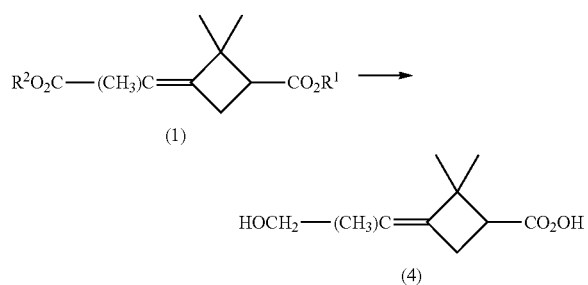

Examples of a reducing agent include hydrogen; borane; alkylborane compounds such as bis(3-methyl-2-butyl)borane; alkylsilane compounds such as triethylsilane; metal hydrides such as aluminum hydride; alkyl metal hydrides such as diisobutylaluminum hydride; complex hydrides such as sodium borohydride, lithium borohydride, potassium borohydride, calcium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tert-butoxyaluminum hydride, sodium bis(2-methoxyethoxy)aluminum hydride; and alkoxy or alkyl derivatives thereof.

The reducing agent may be used alone or in combination thereof. The reducing agent may be commercially available one.

An amount of the reducing agent used is preferably from 3.5 to 100.0 mol, more preferably from 3.6 to 20.0 mol, and even more preferably from 3.7 to 15.0 mol, in terms of hydride, per mol of the diester compound (1), having a dimethylcyclobutane ring.

Examples of a solvent used in the reduction reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 20,000 g per mol of the diester compound (1), having a dimethylcyclobutane ring.

A reaction temperature is preferably from −78 to 180° C., more preferably from −78 to 160° C., and even more preferably from −78 to 140° C.

A reaction time in the aforesaid reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

Examples of the diol compound (4), having a dimethylcyclobutane ring, include (S,Z)-2-(3-hydroxymethyl-2,2-dimethylcyclobutylidene)propan-1-ol of the monitoring formula (4-1), (R,Z)-2-(3-hydroxymethyl-2,2-dimethylcyclobutylidene)propan-1-ol of the monitoring formula (4-2), (S,E)-2-(3-hydroxymethyl-2,2-dimethylcyclobutylidene) propan-1-al of the following formula (4-3), (R,E)-2-(3-hydroxymethyl-2,2-dimethylcyclobutylidene)propan-1-ol of the following formula (4-4), and the racemates, diastereomeric mixtures and scalemic mixtures thereof.

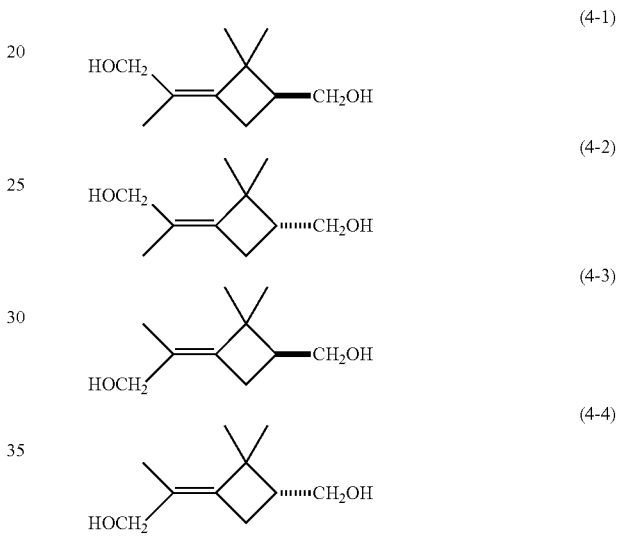

[IV] Process for Preparing the Dimethylcyclobutane Compound (5)

Next, a process according to the following chemical reaction formula for preparing the dimethylcyclobutane compound (5) will be explained hereinafter. The method comprises changing a hydroxyl group in the moiety of HOCH$_2$—(CH$_3$)C= and optionally a hydroxyl group in the moiety of —CH$_2$OH in the diol compound (4), having a dimethylcyclobutane ring, to another group.

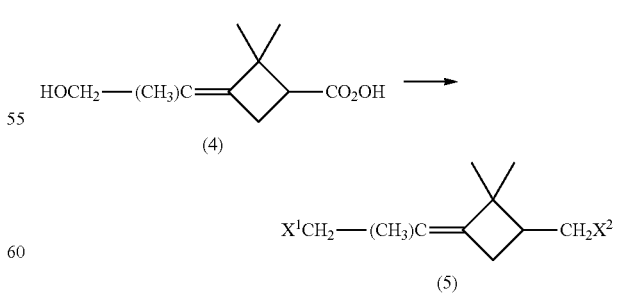

Examples of X$^1$ include an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, a trialkylphosphonio group having 3 to 30 carbon atoms, a triarylphosphonio group having 12 to 30 carbon atoms and a halogen atom. Examples of a halogen atom include a chlorine atom, a bromine atom, and an iodine atom.

Examples of $X^2$ include a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atoms, an alkoxy group having 1 to 12 carbon atoms, an aryloxy group having 6 to 12 carbon atoms, a silyloxy group having 3 to 20 carbon atoms, and a halogen atom. Examples of a halogen atom include a chlorine atom, a bromine atom, and an iodine atom.

Examples of the acyloxy group having 1 to 10 carbon atoms including a carbon atom of a carbonyl group include linear aliphatic acyloxy groups such as a formyloxy group, an acetoxy group, a propanoyloxy group, a butanoyloxy group, a pentanoyloxy group, a hexanoyloxy group, a heptanoyloxy group, an octanoyloxy group, a nonanoyloxy group, a decanoyloxy group, and a crotonyloxy group; aliphatic acyloxy groups such as a 2-methylpropanoyloxy group, a pivaloyloxy group, a 2-methylbutanoyloxy group, a 3-methyl-2-butenoyloxy group, and a 3-methyl-3-butenoyloxy group; halogenated acyloxy groups such as trichloroacetoxy group and a trifluoroacetoxy group; and aromatic acyloxy groups such as a benzoyloxy group; and further may include an acyloxy group having an isomeric relation with the groups above. A part of the hydrogen atoms of these acyloxy groups may be substituted with a methyl group, an ethyl group or a halogen atom. Examples of a halogen atom include a chlorine atom, a bromine atom, and an iodine atom.

Particularly preferred examples of the acyloxy group having 1 to 10 carbon atoms including a carbon atom of a carbonyl group include a formyloxy group, an acetoxy group, a propanoyloxy group, a pivaloyloxy group, a 2-methylbutanoyloxy group, and a benzoyloxy group in view of the availability.

Examples of the alkoxycarbonyloxy group having 2 to 10 carbon atoms including a carbon atom of a carbonyl group include linear saturated alkoxycarbonyloxy groups such as a methoxycarbonyloxy group, an ethoxycarbonyloxy group, an n-propoxycarbonyloxy group, an n-butoxycarbonyloxy group, an n-pentyloxycarbonyloxy group, an n-hexyloxycarbonyloxy group, an n-heptyl oxycarbonyloxy group, an n-octyloxycarbonyloxy group, an n-nonyloxycarbonyloxy group, and an n-decyloxycarbonyloxy group; branched saturated alkoxycarbonyloxy groups such as an isopropoxycarbonyloxy group and a t-butoxycarbonyloxy group; linear unsaturated alkoxycarbonyloxy groups such as a 2-propenyloxycarbonyloxy group and a 2-propynyloxycarbonyloxy group; branched unsaturated alkoxycarbonyloxy groups such as a 2-methyl-2-propenyloxycarbonyloxy group; cyclic alkoxycarbonyloxy groups such as a cyclopropyloxycarbonyloxy group, a 2-methylcyclopropyloxycarbonyloxy group, a cyclobutyloxycarbonyloxy group, and a cyclopentyloxycarbonyloxy group; alkoxycarbonyloxy groups having an aromatic ring such as a benzyloxycarbonyloxy group and a paramethoxybenzyloxycarbonyloxy group; oxyalkoxycarbonyloxy groups such as a methoxymethycarbonyloxy group, a benzyloxymethoxycarbonyloxy group, and a paramethoxybenzyloxymethoxycarbonyloxy group; and halogenated alkoxycarbonyloxy groups such as a 2,2,2-trichloroethoxycarbonyloxy group; and further may include an alkoxycarbonyloxy group having an isomeric relation with the groups above. A part of the hydrogen atoms of these alkoxycarbonyloxy groups may be substituted with a methyl group, an ethyl group or a halogen atom. Examples of a halogen atom include a chlorine atom, a bromine atom, and an iodine atom.

Particularly preferred examples of the alkoxycarbonyloxy group having 2 to 10 carbon atoms including a carbon atom of a carbonyl group include a methoxycarbonyloxy group, an ethoxycarbonyloxy group, and an n-propoxycarbonyloxy group in view of the availability.

Examples of the alkanesulfonyloxy group having 1 to 10 carbon atoms include a methanesulfonyloxy group, an ethanesulfonyloxy group, a 1-butanesulfonyloxy group, a 1-pentanesulfonyloxy group, a 1-hexanesulfonyloxy group, a 1-heptanesulfonyloxy group, a 1-octanesulfonyloxy group, a 1-nonanesulfonyloxy group, a 1-decanesulfonyloxy group, an allylsulfonyloxy group, a 10-camphorsulfonyloxy group, a trifluoromethanesulfonyloxy group, and an α-benzylsulfonyloxy group; and further may include an alkanesulfonyloxy group having an isomeric relation with the groups above. A part of the hydrogen atoms of these alkanesulfonyloxy groups may be substituted with a methyl group, an ethyl group or a halogen atom. Examples of a halogen atom include a chlorine atom, a bromine atom, and an iodine atom.

Particularly preferred examples of the alkanesulfonyloxy group having 1 to 10 carbon atoms include a methanesulfonyloxy group and an ethanesulfonyloxy group in view of the availability.

Examples of the arenesulfonyloxy group having 6 to 20 carbon atoms include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a paratoluenesulfonyloxy group, a 1-naphthalenesulfonyloxy group, and a 2-naphthalenesulfonyloxy group; and further may include an arenesulfonyloxy group having an isomeric relation with the groups above. A part of the hydrogen atoms of these arenesulfonyloxy groups may be substituted with a methyl group, an ethyl group or a halogen atom. Examples of a halogen atom include a chlorine atom, a bromine atom, and an iodine atom.

Particularly preferred examples of the arenesulfonyloxy group having 6 to 20 carbon atoms include a benzenesulfonyloxy group and a paratoluenesulfonyloxy group in view of the availability.

Examples of the alkoxy group having 1 to 12 carbon atoms include linear saturated alkoxy groups such as a methoxy group, an ethoxy group, an n-propoxy group, an n-butoxy group, an n-pentyloxy group, an n-hexyloxy group, an n-heptyloxy group, an n-octyloxy group, an n-nonyloxy group, an n-decyloxy group, an n-undecyloxy group, and an n-dodecyloxy group; branched saturated alkoxy groups such as an isopropoxy group, an isobutyloxy group, and a t-butoxy group; linear unsaturated alkoxy groups such as a 2-propenyloxy group and a 2-propynyloxy group; branched unsaturated alkoxy groups such as a 2-methyl-2-propenyloxy group; cyclic alkoxy groups such as a cyclopropyloxy group, a 2-methylcyclopropyloxy group, a cyclobutyloxy group, and a cyclopentyloxy group; alkoxy groups having an aromatic ring such as a benzyloxy group and a paramethoxybenzyloxy group; oxyalkoxy groups such as a methoxymethoxy group, a 2-methoxyethoxymethoxy group, a benzyloxymethoxy group, a paramethoxybenzyloxymethoxy group, a 1-ethoxyethoxy group, a 1-allyloxyethoxy group, and a tetrahydropyran-2-yloxy group; and halogenated alkoxy groups such as a 2,2,2-trichloroethoxy group and a pentafluoroethoxy group; and further may include an alkoxy group having an isomeric relation with the groups above. A part of the hydrogen atoms of these alkoxy groups may be substituted with a methyl group, an ethyl group or a halogen atom. Examples of a halogen atom include a chlorine atom, a bromine atom, and an iodine atom.

Particularly preferred examples of the alkoxy group having 1 to 12 carbon atoms include a methoxy group, an ethoxy group, a 2-propenyloxy group, a methoxymethoxy group, a 1-ethoxyethoxy group, a 1-allyloxyethoxy group, and a tetrahydropyran-2-yloxy group in view of ease of the preparation.

Examples of the aryloxy group having 6 to 12 carbon atoms include a phenoxy group, a 4-chlorophenoxy group, a 4-methoxyphenoxy group, a naphthoxy group, and a 4-biphenyloxy group; and further may include an aryloxy group having an isomeric relation with the groups above. A part of the hydrogen atoms of these aryloxy groups may be substituted with a methyl group, an ethyl group or a halogen atom. Examples of a halogen atom include a chlorine atom, a bromine atom, and an iodine atom.

Particularly preferred examples of the aryloxy group having 6 to 12 carbon atoms include a phenoxy group and a naphthoxy group in view of the availability.

Examples of a silyloxy group having 3 to 20 carbon atoms include trialkylsilyloxy groups such as a trimethylsilyloxy group, a triethylsilyloxy group, a triisopropylsilyloxy group, and a t-butyldimethylsilyloxy group; monoalkyldiarylsilyloxy groups such as a t-butyldiphenylsilyloxy group; and further may include a silyloxy group having an isomeric relation with the groups above. A part of the hydrogen atoms of these silyloxy groups having 3 to 20 carbon atoms may be substituted with a methyl group, an ethyl group or a halogen atom. Examples of a halogen atom include a chlorine atom, a bromine atom, and an iodine atom.

Particularly preferred examples of a silyloxy group having 3 to 20 carbon atoms include a trimethylsilyloxy group, a triethylsilyloxy group, a triisopropylsilyloxy group, and a t-butyldimethylsilyloxy group in view of the availability.

Examples of a trialkylphosphonio group having 3 to 30 carbon atoms include a trimethylphosphonio group, a triethylphosphonio group, a tripropylphosphonio group, a tributylphosphonio group, a tripentylphosphonio group, a trihexylphosphonio group, a triheptylphosphonio group, a trioctylphosphonio group, a trinonylphosphonio group, a tridecylphosphonio group, and a tricyclohexylphosphonio group.

Particularly preferred examples of a trialkylphosphonio group having 3 to 30 carbon atoms include a tributylphosphonio group, a tricyclohexylphosphonio group, and a trioctylphosphonio group in view of the availability.

Examples of a triarylphosphonio group having 12 to 30 carbon atoms include a triphenylphosphonio group, a tri(2-methylphenyl)phosphonio group, a trifurylphosphonio group, and a tri(1-naphthyl)phosphonio group.

Particularly preferred examples of a triarylphosphonio group having 12 to 30 carbon atoms include a triphenylphosphonio group and a tri (2-methylphenyl)phosphonio group in view of the availability.

Examples of a halogen atom include a chlorine atom, a bromine atom, and an iodine atom. Particularly preferred examples of a halogen atom include a chlorine atom and a bromine atom in view of the availability.

Examples of the dimethylcyclobutane compound (5) include a dimethylcyclobutane compound having two acyloxy groups, a dimethylcyclobutane compound having two halogen atoms, a dimethylcyclobutane compound having a phosphonio group and a hydroxyl group, and a dimethylcyclobutane compound having a halogen atom and an acyloxy group.

Examples of the dimethylcyclobutane compound having two acyloxy groups include [3-(2-acyloxy-1-methylethylidene)-2,2-dimethylcyclobutyl]methyl acylate compounds such as [3-(2-acetoxy-1-methylethylidene)-2,2-dimethylcyclobutyl]methyl acetate and [3-[2-(2-methylbutanoyloxy)-1-methylethylidene]-2,2-dimethylcyclobutyl]methyl 2-methylbutanoate.

Examples of the dimethylcyclobutane compound having two halogen atoms include 1-halomethyl-3-(2-halo-1-methylethylidene)-2,2-dimethylcyclobutane compounds such as 1-chloromethyl-3-(2-chloro-1-methylethylidene)-2,2-dimethylcyclobutane.

Examples of the dimethylcyclobutane compound having a phosphonio group and a hydroxyl group include [2-(3-hydroxymethyl-2,2-dimethylcyclobutylidene)propyl]triphenylphosphonium compounds such as [2-(3-hydroxymethyl-2,2-dimethylcyclobutylidene)propyl] triphenylphosphonium.

Examples of the dimethylcyclobutane compound having a halogen atom and an acyloxy group include [2,2-dimethyl-3-(2-halo-1-methylethylidene)cyclobutyl]methyl acylate compounds such as [2,2-dimethyl-3-(2-bromo-1-methylethylidene)cyclobutyl]methyl acetate.

The aforesaid reaction for changing a hydroxyl group to another group may be carried out by a known method.

For instance, a dimethylcyclobutane compound of the following general formula (5A), having two acyloxy groups may be produced by subjecting the diol compound (4) having a dimethylcyclobutane ring to an acylation reaction with an acylating agent, as shown in the following chemical reaction formula (see Examples 3 and 4 below).

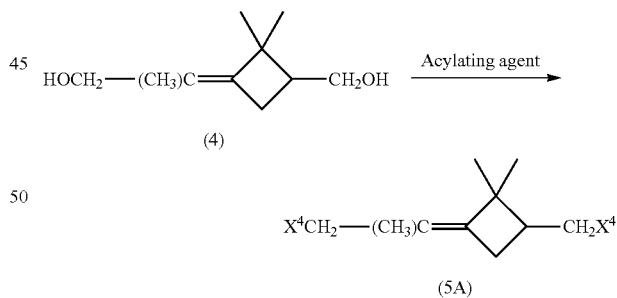

$X^4$ represents an acyloxy group having 1 to 10 carbon atoms including a carbon atom of a carbonyl group. Examples of $X^4$ are the acyloxy group having 1 to 10 carbon atoms defined for $X^1$ and $X^2$ above.

Examples of an acylating agent include acid anhydrides such as acetic anhydride, propionic anhydride, butanoic anhydride, and 2-methylbutanoic anhydride; and acid chlorides such as acetyl chloride, propionyl chloride, butanoyl chloride, and 2-methylbutanoyl chloride.

The acylating agent may be used alone or in combination thereof. The acylating agent may be commercially available one.

An amount of the acylating agent used is preferably from 1.4 to 100 mol, more preferably from 1.6 to 50 mol, and even more preferably from 1.8 to 20 mol, per mol of the diol compound (4), having a dimethylcyclobutane ring.

Examples of a base used in the acylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 1.5 to 110 mol, more preferably from 1.7 to 60 mol, and even more preferably from 1.9 to 30 mol, per mol of the diol compound (4), having a dimethylcyclobutane ring.

Examples of a solvent used in the acylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the diol compound (4), having a dimethylcyclobutane ring.

A reaction temperature in the acylation reaction is preferably from −78 to 180° C., more preferably from −60 to 160° C., and even more preferably from −40 to 140° C. A reaction time in the aforesaid reaction may be set arbitrarily. It is desirable in view of the yield to monitor the reaction with gas chromatography (GC) or silica gel thin layer chromatography (LC) to confirm the completion of the reaction. A reaction time is usually about 0.5 to 24 hours.

The dimethylcyclobutane compound of the following general formula (5B), having two halogen atoms, may be produced by subjecting the diol compound (4), having a dimethylcyclobutane ring, to a halogenation reaction with a halogen source and a phosphine compound, as shown in the following chemical reaction formula (see Example 5 below).

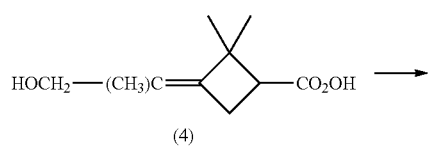

(4)

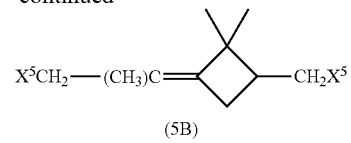

(5B)

$X^5$ represents a halogen atom. Examples of a halogen atom include a chlorine atom, a bromine atom, and an iodine atom. $X^5$ is derived from the halogen source used in the halogenation reaction.

Examples of a halogen source include carbon tetrahalide compounds such as carbon tetrachloride and carbon tetrabromide; and halogen molecules such as bromine and iodine.

The halogen source may be used alone or in combination thereof. The halogen source may be commercially available one.

An amount of the halogen source used is preferably from 1.4 to 1,000 mol, more preferably from 1.6 to 500 mol, and even more preferably from 1.8 to 200 mol, per mol of the diol compound (4), having a dimethylcyclobutane ring.

Examples of a phosphine compound include triarylphosphine compounds such as triphenylphosphine; and trialkylphosphine compounds such as trioctylphosphine.

The phosphine compound may be used alone or in combination thereof. The phosphine compound may be commercially available one.

An amount of the phosphine compound used is preferably from 1.4 to 20.0 mol, more preferably from 1.6 to 16 mol, and even more preferably from 1.8 to 14 mol, per mol of the diol compound (4), having a dimethylcyclobutane ring.

The halogenation reaction may be carried out in the presence of a base.

Examples of a base include organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0 to 1000 mol, more preferably from 0 to 500 mol, and even more preferably from 0 to 200 mol, per mol of the diol compound (4), having a dimethylcyclobutane ring.

Examples of a solvent used in the halogenation reaction include ethers such as diethyl ether, dibutyl ether, tetrahydrofuran, 1,4-dioxane; hydrocarbons such as hexane, heptane, benzene, toluene, xylene, and cumene; chloride solvents such as methylene chloride, chloroform, carbon tetrachloride, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; and esters such as ethyl acetate and n-butyl acetate.

The solvent may be used alone or in combination thereof. The solvent may be commercially available one.

An amount of the solvent used is preferably from 0 to 20,000 g per mol of the diol compound (4), having a dimethylcyclobutane ring.

A reaction temperature in the halogenation reaction is preferably from −78 to 180° C., more preferably from −60 to 160° C., and even more preferably from −40 to 140° C.

A reaction time in the halogenation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

The dimethylcyclobutane compound of the following general formula (5C), having a phosphonio group and a hydroxyl group, may be produced by subjecting the diol compound (4), having a dimethylcyclobutane ring, to a phosphonation reaction with a phosphine hydrohalide, as shown in the following chemical reaction formula (see Example 6 below).

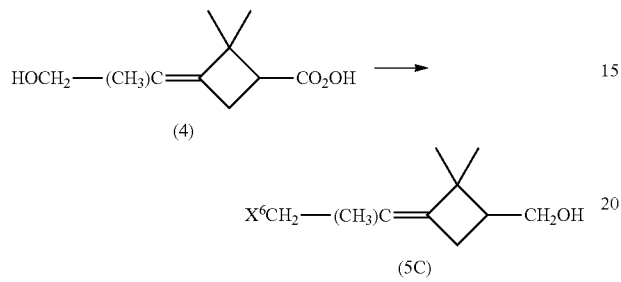

$X^1$ represents a trialkylphosphonio group having 3 to 30 carbon atoms or a triarylphosphonio group having 12 to 30 carbon atoms.

Examples of the trialkylphosphonio group having 3 to 30 carbon atoms are as mentioned for $X^1$.

Examples of the triarylphosphonio group having 12 to 30 carbon atoms include the groups mentioned above in a case where $X^1$ is a triarylphosphonio group having 12 to 30 carbon atoms. $X^6$ is derived from the phosphine hydrohalide used in the phosphonation reaction.

Examples of the phosphine hydrohalide include triphenylphosphine hydrochloride, triphenylphosphine hydrobromide, and triphenylphosphine hydroiodide.

The phosphine hydrohalide may be used alone or in combination thereof. The phosphine hydrohalide may be commercially available one.

An amount of the phosphine hydrohalide used is preferably from 0.7 to 10.0 mol, more preferably from 0.8 to 8.0 mol, and even more preferably from 0.9 to 6.0 mol, per mol of the diol compound (4), having a dimethylcyclobutane ring.

Examples of a solvent used in the phosphonation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of the diol compound (4), having a dimethylcyclobutane ring.

A reaction temperature in the phosphonation reaction is preferably from −78 to 180° C., more preferably from −60 to 160° C., and even more preferably from −40 to 140° C.

A reaction time in the phosphonation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

The hydroxyl groups in the diol compound, having a dimethylcyclobutane ring, (4) may be changed in multiple steps.

For instance, a dimethylcyclobutane compound of the following general formula (5D), having a halogen atom and an acyloxy group, may be produced by halogenating the aforesaid dimethylcyclobutane compound (A), having two acyloxy groups, with a hydrogen halide compound, as shown in the following chemical reaction formula (see Example 7 below).

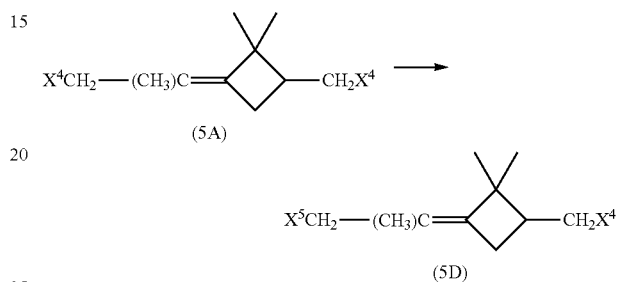

$X^4$ and $X^5$ in the dimethylcyclobutane compound (5D), having a halogen atom and an acyloxy group, are as defined above.

Examples of a hydrogen halide compound include hydrogen chloride, hydrogen bromide, and hydrogen iodide.

The hydrogen halide compound may be used alone or in combination thereof. The hydrogen halide may be commercially available one.

An amount of the hydrogen halide compound used is preferably from 0.7 to 10 mol, more preferably from 0.8 to 8 mol, and even more preferably from 0.9 to 6 mol, per mol of the dimethylcyclobutane compound (5A), having two acyloxy groups.

Examples of solvent used in the halogenation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, tetrachloromethane, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; carboxylic acids such as formic acid, acetic acid, and propionic acid; and water.

The solvent may be used alone or in combination thereof. The solvent may be commercially available one.

An amount of the solvent used is preferably from 10 to 10,000 g per mol of the dimethylcyclobutane compound (5A), having two acyloxy groups.

A reaction temperature in the halogenation reaction is preferably from −78 to 180° C., more preferably from −60 to 160° C., and even more preferably from −40 to 140° C.

A reaction time in the halogenation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

Examples of the dimethylcyclobutane compound (5) include a (S,Z) form of the dimethylcyclobutane compound of the general following formula (5-1), a (R,Z) form of the dimethylcyclobutane compound of the general following formula (5-2), a (S,E) form of the dimethylcyclobutane compound of the general following formula (5-3), and a (R,E) form of the dimethylcyclobutane compound of the general following formula (5-4), and the racemates, diastereomeric mixtures and scalemic mixtures thereof.

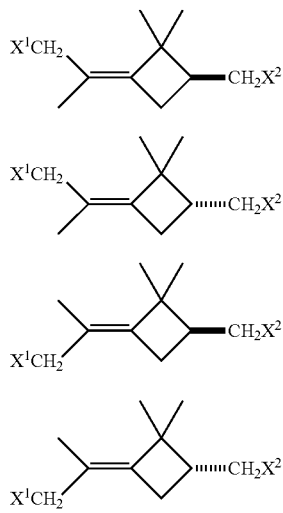

[V] Process for Preparing the Isopropenyl Dimethylcyclobutane Compound (6) and the Isopropylidene Dimethylcyclobutane Compound (7).

Next, a process for preparing the isopropenyl dimethylcyclobutane compound of the following general formula (6) and the isopropylidene dimethylcyclobutane compound of the following formula (7) will be explained hereinafter. The method comprises subjecting the dimethylcyclobutane compound (5) to a reduction reaction to produce the isopropenyl dimethylcyclobutane compound (6) and/or the isopropylidene dimethylcyclobutane compound (7). The reduction reaction is carried out, if necessary, using a reducing agent in the presence of a metal catalyst and a ligand.

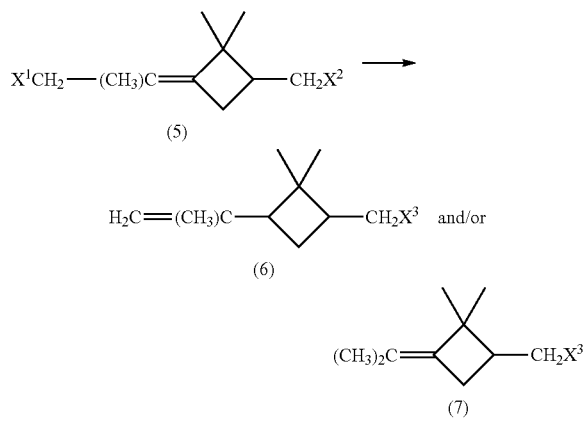

$X^3$ represents a hydroxyl group, an acyloxy group having 1 to 10 carbon atoms including a carbon atom of a carbonyl group, an alkoxycarbonyloxy group having 2 to 10 carbon atoms including a carbon atom of a carbonyl group, an alkanesulfonyloxy group having 1 to 10 carbon atoms, an arenesulfonyloxy group having 6 to 20 carbon atom, an alkoxy group having 1 to 12 carbon atoms, an aryloxy group having 6 to 12 carbon atoms, a silyloxy group having 3 to 20 carbon atoms, or a halogen atom. Each of $X^3$ may be same as $X^1$ and $X^2$. In the reduction reaction above, in a case where $X^2$ in the dimethylcyclobutane compound (5) is maintained, $X^2$ is same as $X^3$ after the reaction. Meanwhile in a case where $X^2$ is not maintained, $X^2$ is different from $X^3$ after the reaction.

Examples of a reducing agent include hydrogen; formic acid and formates such as sodium formate, ammonium formate and triethylammonium formate; borane; alkylborane compounds such as bis(3-methyl-2-butyl)borane; alkylsilane compounds such as triethylsilane; metal hydrides such as aluminum hydride; alkyl metal hydrides such as diisobutylaluminum hydride; complex hydrides such as sodium borohydride, lithium borohydride, potassium borohydride, calcium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-tert-butoxyaluminum hydride, sodium bis(2-methoxyethoxy)aluminum hydride; and alkoxy or alkyl derivatives thereof.

The reducing agent may be used alone or in combination thereof. The reducing agent may be commercially available one.

An amount of the reducing agent used is preferably from 0.7 to 100.0 mol, more preferably from 0.8 to 80.0 mol, and even more preferably from 0.9 to 60.0 mol, in terms of hydride per mol of the dimethylcyclobutane compound (5).

The reduction reaction may be carried out in the presence of a metal catalyst.

Examples of a metal catalyst include a palladium catalyst, a nickel catalyst, an iron catalyst, a cobalt catalyst, a molybdenum catalyst, a tungsten catalyst, a rhodium catalyst, an iridium catalyst, with a palladium catalyst being preferable in view of the yield and selectivity.

Examples of a palladium catalyst include zero-valent palladium catalysts such as tetrakis(triphenylphosphine)palladium and bis(dibenzylideneacetone)palladium catalyst; and divalent palladium catalysts such as palladium acetate, bis(triphenylphosphine)palladium diacetate, palladium trifluoroacetate, palladium chloride, bis(triphenylphosphine) palladium dichloride, allyl palladium chloride, and bis(2,4-pentanedionato)palladium.

The metal catalyst may be used alone or in combination thereof. The metal catalyst may be commercially available one.

An amount of the metal catalyst used is preferably from 0.0001 to 1 mol, more preferably from 0.0002 to 0.9 mol, and even more preferably from 0.0003 to 0.8 mol, per mol of the dimethylcyclobutane compound (5).

A ligand may be used together with the metal catalyst, if necessary.

Examples of a ligand include phosphite ester compounds such as triethyl phosphite and triphenyl phosphite, tributylphosphine, tricyclohexylphosphine, trioctylphosphine, triphenylphosphine; phosphine compounds such as tributylphosphine, tricyclohexylphosphine, trioctylphosphine, triphenylphosphine, 2,2'-bis(diphenylphosphino)-1, 1'-binaphthyl (BINAP), and 2-(di-tert-butylphosphino)biphenyl (i.e., 2-biphenylyl)di-tert-butylphosphine); acetone derivatives such as acetylacetone and dibenzylideneacetone; nitrile compounds such as acetonitrile and benzonitrile; nitrogen-containing compounds such as dimethylimidazolidinone, ethylenediamine, and hexamethylphosphoric triamide; and diene compounds such as 1,5-cyclooctadiene and 2,5-norbornadiene.

The ligand may be used alone or in combination thereof. The ligand may be commercially available one.

An amount of the ligand used is preferably from 0.001 to 10,000 mol, more preferably from 0.01 to 1,000 mol, and even more preferably from 0.1 to 100 mol, per mol of the metal catalyst.

Examples of s solvent used in the reduction reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; ketones such as acetone and 2-butanone; and water.

The solvent may be used alone or in combination thereof. The solvent may be commercially available one.

An amount of the solvent used is preferably from 10 to 150,000 g per mol of the dimethylcyclobutane compound (5).

A reaction temperature in the reduction reaction is preferably from −78 to 180° C., more preferably from −60 to 160° C., and even more preferably from −40 to 140° C.

A reaction time in the reduction reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 30 hours.

Examples of the isopropenyl dimethylcyclobutane compound (6) include a (1R,3R)-3-isopropenyl-2,2-dimethylcyclobutane compound of the following general formula (6-1), a (1S,3S)-3-isopropenyl-2,2-dimethylcyclobutane compound of the following general formula (6-2), a (1R,3S)-3-isopropenyl-2,2-dimethylcyclobutane 16 compound of the following general formula (6-3) and a (1S,3R)-3-isopropenyl-2,2-dimethylcyclobutane compound of the following general formula (6-4), and the racemates, diastereomeric mixtures and scalemic mixtures thereof.

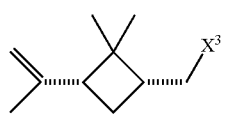

(6-1)

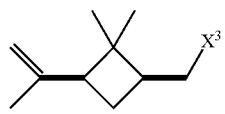

(6-2)

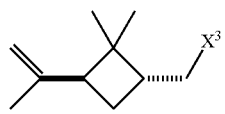

(6-3)

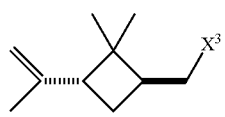

(6-4)

Examples of the isopropenyl dimethylcyclobutane compound (6) include an isopropenyl dimethylcyclobutane compound having an acyloxymethyl group, an isopropenyl dimethylcyclobutane compound having a halomethyl group, an isopropenyl dimethylcyclobutane compound having a hydroxymethyl group, and an isopropenyl dimethylcyclobutane compound having an alkanesulfonyloxymethyl group.

Examples of the isopropenyl dimethylcyclobutane compounds having an acyloxymethyl group include (3-isopropenyl-2,2-dimethylcyclobutyl) methyl acylate compounds such as (3-isopropenyl-2,2-dimethylcyclobutyl)methyl acetate, (3-isopropenyl-2,2-dimethylcyclobutyl)methyl 2-methylbutanoate, and (3-isopropenyl-2,2-dimethylcyclobutyl)methyl 3-methyl-3-butenoate.

Examples of the isopropenyl dimethylcyclobutane compound having a halomethyl group include 1-halomethyl-3-isopropenyl-2,2-dimethylcyclobutane compounds such as 1-chloromethyl-3-isopropenyl-2,2-dimethylcyclobutane.

Examples of the isopropenyl dimethylcyclobutane compound having a hydroxymethyl group include (3-isopropenyl-2,2-dimethylcyclobutyl) methanol.

Examples of the isopropenyl dimethylcyclobutane compound having an alkanesulfonyloxymethyl group include (3-isopropenyl-2,2-dimethylcyclobutyl)methyl alkanesulfonate compounds such as (3-isopropenyl-2,2-dimethylcyclobutyl)methyl methanesulfonate.

Examples of the isopropylidene dimethylcyclobutane compound (7) include a (1R)-3-isopropylidene-2,2-dimethylcyclobutane compound of the following general formula (7-1), a (1S)-3-isopropylidene-2,2-dimethylcyclobutane compound of the following general formula (7-2), and the racemates and scalemic mixtures thereof.

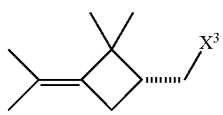

(7-1)

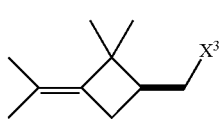

(7-2)

Examples of the isopropylidene dimethylcyclobutane compound (7) include an isopropylidene dimethylcyclobutane compound having an acyloxymethyl group, an isopropylidene dimethylcyclobutane compound having a halomethyl group, an isopropylidene dimethylcyclobutane compound having a hydroxymethyl group, and an isopropylidene dimethylcyclobutane compound having an alkanesulfonyloxymethyl group.

Examples of the isopropylidene dimethylcyclobutane compound having an acyloxymethyl group include (3-isopropylidene-2,2-dimethylcyclobutyl)methyl acylate compounds such as (3-isopropylidene-2,2-dimethylcyclobutyl) methyl acetate, (3-isopropylidene-2,2-dimethylcyclobutyl) methyl 2-methylbutanoate, and (3-isopropylidene-2,2-dimethylcyclobutyl)methyl 3-methyl-2-butenoate.

Examples of the isopropylidene dimethylcyclobutane compound having a halomethyl group include 1-halomethyl-3-isopropylidene-2,2-dimethylcyclobutane compounds such as 1-chloromethyl-3-isopropylidene-2,2-dimethylcyclobutane.

Examples of the isopropylidene dimethylcyclobutane compound having a hydroxymethyl group include (3-isopropylidene-2,2-dimethylcyclobutyl)methanol.

Examples of the isopropylidene dimethylcyclobutane compound having an alkanesulfonyloxymethyl group include (3-isopropylidene-2,2-dimethylcyclobutyl)methyl alkanesulfonate compounds such as (3-isopropylidene-2,2-dimethylcyclobutyl)methyl methanesulfonate.

The isopropenyl dimethylcyclobutane compound of the following general formula (6A), having an acyloxymethyl group, and the isopropylidene dimethylcyclobutane compound of the following general formula (7A) may be produced by subjecting the dimethylcyclobutane compound (5A), having two acyloxy groups, to a reduction reaction, as shown in the following chemical reaction formula (see Examples 8, 9, 10, 11 and 12 below). The reduction reaction may be carried out, if necessary, using a reducing agent in the presence of a metal catalyst and a ligand.

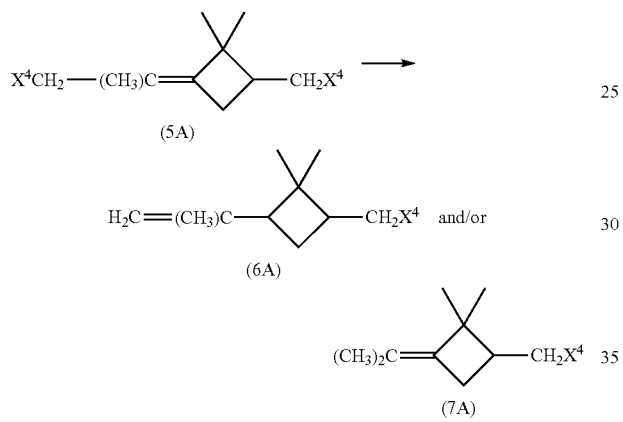

$X^4$ in the isopropenyl dimethylcyclobutane compound (6A), having an acyloxymethyl group, and the isopropylidene dimethylcyclobutane compound (7A) is as defined above.

The isopropenyl dimethylcyclobutane compound of the following general formula (6B), having a halomethyl group, and the isopropylidene dimethylcyclobutane compound of the following general formula (7B) may be produced by subjecting the dimethylcyclobutane compound (5B), having two halogen atoms, to a reduction reaction, as shown in the following chemical reaction formula (see Example 13 below). The reduction reaction may be carried out, if necessary, using a reducing agent in the presence of a metal catalyst and a ligand.

$X^3$ in the isopropenyl dimethylcyclobutane compound (6B), having a halomethyl group, and the isopropylidene dimethylcyclobutane compound (7B) is as defined above.

For instance, the isopropenyl dimethylcyclobutane compound of the following formula (6C), having a hydroxymethyl group, and the isopropylidene dimethylcyclobutane compound of the following formula (7C) may be produced by subjecting the dimethylcyclobutane compound (5C), having a phosphonio group and a hydroxyl group, to a reduction reaction, as shown in the following chemical reaction formula (see Example 14 below). The reduction reaction may be carried out, if necessary, using a reducing agent in the presence of a metal catalyst and a ligand.

The isopropenyl dimethylcyclobutane compound (6C), having a hydroxymethyl group, and the isopropylidene dimethylcyclobutane compound (7C) may be produced by subjecting the dimethylcyclobutane compound (5D), having a halogen atom and an acyloxy group, to a reduction reaction, as shown in the following chemical reaction formula (see Example 15 below). The reduction react and/or be carried out, if necessary, using a reducing agent in the presence of a metal catalyst and a ligand.

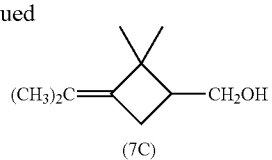

(7C)

If necessary, the isopropenyl dimethylcyclobutane compound (6'), having a certain group $X^3$, and/or the isopropylidene dimethylcyclobutane compound (7'), having a certain group $X^3$, may be obtained by changing $X^3$ in the isopropenyl dimethylcyclobutane compound (6) and/or the isopropylidene dimethylcyclobutane compound (7) to the certain group $X^3$, wherein options for $X^3$ are as defined above (see Example 21 below). Changing of the group may be carried out by a known method.

The isopropenyl dimethylcyclobutane compound having an acyloxymethyl group (6A) and the isopropylidene dimethylcyclobutane compound (7A) may be produced by subjecting the isopropenyl dimethylcyclobutane compound (6B), having a halomethyl group, and/or the isopropylidene dimethylcyclobutane compound (7B) to an acyloxylation reaction with a carboxylate salt, as shown in the following chemical reaction formula (see Example 16 below).

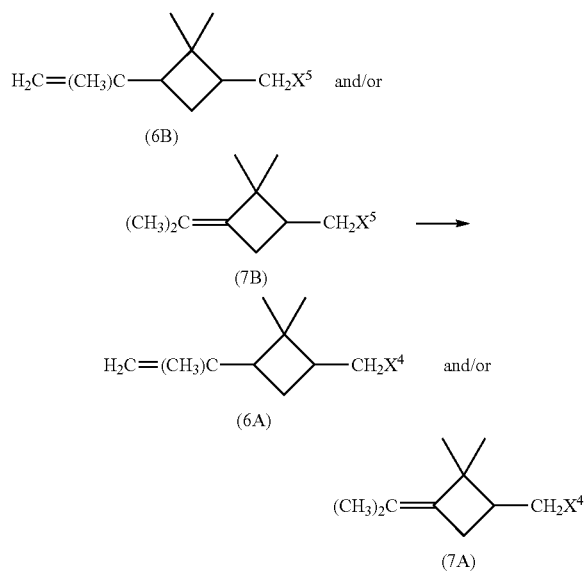

The chemical reaction formula shows the production of a mixture of the compounds (6A) and (7A) from a mixture of the compounds (6B) and (7B), the production of the compound (6A) from the compound (6B), and the production of the compound (7A) from the compound (713).

Examples of a carboxylate salt include metal carboxylates such as lithium acetate, sodium acetate, potassium acetate, cesium acetate, magnesium acetate, and calcium acetate; and ammonium carboxylates such as ammonium acetate and tetrabutylammonium acetate.

The carboxylate salt may be used alone or in combination thereof. The carboxylate may be commercially available one.

The carboxylate salt may be prepared in a reaction system by reacting a carboxylic acid with a base such as sodium hydroxide, potassium carbonate and tetrabutylammonium hydroxide.

An amount of the carboxylate salt used is preferably from 0.7 to 10 mol, more preferably from 0.8 to 8 mol, and even more preferably from 0.9 to 6 mol, per mol of a total of the isopropenyl dimethylcyclobutane compound (6B), having a halomethyl group, and the isopropylidene dimethylcyclobutane compound (7B).

The acyloxylation reaction may be carried out in the presence of a halide.

Examples of a halide include metal halides such as lithium iodide, sodium iodide, potassium iodide, cesium iodide, magnesium iodide, calcium iodide, lithium bromide, sodium bromide, potassium bromide, cesium bromide, magnesium bromide, and calcium bromide; ammonium halide compounds such as ammonium iodide, ammonium bromide, tetrabutylammonium iodide, tetrabutylammonium bromide, and tetrabutylammonium chloride.

The halide may be used alone or in combination thereof. The halide may be commercially available one.

An amount of the halide used is preferably from 0.0001 to 10 mol, more preferably from 0.0002 to 8 mol, and even more preferably from 0.0003 to 6 mol, per mol of a total of the isopropenyl dimethylcyclobutane compound (6B), having a halomethyl group, and the isopropylidene dimethylcyclobutane compound (7B).

Examples of a solvent used in the acyloxylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylacetamide, N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; ketones such as acetone and 2-butanone; and water.

The solvent may be used alone or in combination thereof. The solvent may be commercially available one.

An amount of the solvent used is preferably from 10 to 10,000 g per mol of a total of the isopropenyl dimethylcyclobutane compound (6B), having a halomethyl group, and the isopropylidene dimethylcyclobutane compound (7B).

A reaction temperature in the acyloxylation reaction is preferably from −78 to 200° C., more preferably from −60 to 180° C., and even more preferably from −40 to 160° C.

A reaction time in the acyloxylation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

The isopropenyl dimethylcyclobutane compound of the following general formula (6A), having an acyloxymethyl group, and the isopropylidene dimethylcyclobutane compound (7A) may be produced by subjecting the isopropenyl dimethylcyclobutane compound (6C), having a hydroxymethyl group, and/or the isopropylidene dimethylcyclobutane compound (7C) to an acylation reaction with an acylating agent, as shown in the following chemical reaction formula (see Examples 17, 18 and 22 below).

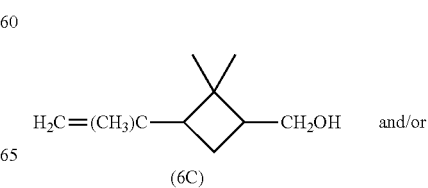

(6C)

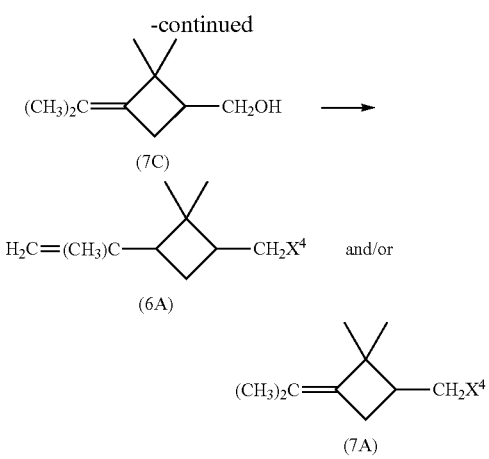

The chemical reaction formula shows the production of a mixture of the compounds (6A) and (7A) from a mixture of the compounds (6C) and (7C), the production of the compound (6A) from the compound (6C), and the production of the compound (7C) from the compound (7A).

Examples of an acylating agent include acid anhydrides such as acetic and/or anhydride; and acid chlorides such as acetyl chloride.

The acylating agent may be used alone or in combination thereof. The acylating agent may be commercially available one.

An amount of the acylating agent used is preferably from 0.7 to 100 mol, more preferably from 0.8 to 50 mol, and even more preferably from 0.9 to 20 mol, per mol of a total of the isopropenyl dimethylcyclobutane compound (6C), having a hydroxymethyl group, and the isopropylidene dimethylcyclobutane compound (7C).

Examples of a base used in the acylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 100 mol, more preferably from 0.8 to 50 mol, and even more preferably from 0.9 to 20 mol, per mol of a total of the isopropenyl dimethylcyclobutane compound (6C), having a hydroxymethyl group, and the isopropylidene dimethylcyclobutane compound (7C).

Examples of a solvent used in the acylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and water.

The solvent may be used alone or in combination thereof. The solvent may be commercially available one.

An amount of the solvent used is preferably from 10 to 15,000 g per mol of a total of the isopropenyl dimethylcyclobutane compound (6C), having a hydroxymethyl group, and the isopropylidene dimethylcyclobutane compound (7C).

A reaction temperature in the acylation reaction is preferably from −78 to 180° C., more preferably from −60 to 160° C., and even more preferably from −40 to 140° C.

A reaction time in the acylation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

The isopropenyl dimethylcyclobutane compound (6D), having an alkanesulfonyloxymethyl group, and the isopropylidene dimethylcyclobutane compound (7D) may be produced by subjecting the isopropenyl dimethylcyclobutane compound (6C), having a hydroxymethyl group, and/or the isopropylidene dimethylcyclobutane compound (7C) to an alkanesulfonylation reaction with an alkane sulfonylating agent, as shown in the following chemical reaction formula (see Example 19 below),

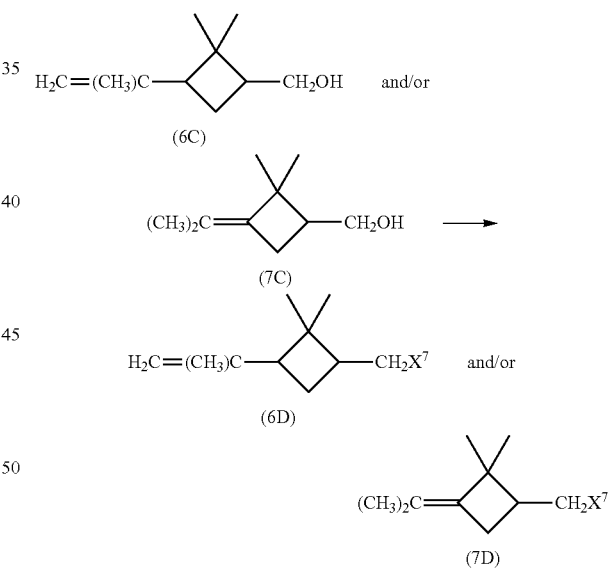

The chemical reaction formula shows the production of a mixture of the compounds (6D) and (7D) from a mixture of the compounds (6C) and (7C), the production of the compound (6D) from the compound (6C), and the production of the compound (7D) from the compound (7C).

$X^7$ in the isopropenyl dimethylcyclobutane compound (6)), having an alkanesulfonyloxymethyl group, and the isopropylidene dimethylcyclobutane compound (71) represents an alkanesulfonyloxy group having 1 to 10 carbon atoms. Examples of the alkanesulfonyloxy group having 1 to 10 carbon atoms include those defined for the groups $X^1$ and $X^2$.

Examples of an alkane sulfonylating agent include alkane sulfonic anhydrides such as a methane sulfonic anhydride; and alkane sulfonyl chlorides such as a methane sulfonyl chloride.

The alkane sulfonylating agent may be used alone or in combination thereof. The alkane sulfonylating agent may be commercially available one.

An amount of the alkane sulfonylating agent used is 0.7 to 100 mol, more preferably from 0.8 to 50 mol, and even more preferably from 0.9 to 20 mol, per mol of a total of the isopropenyl dimethylcyclobutane compound (6C), having a hydroxymethyl group, and the isopropylidene dimethylcyclobutane compound (7C).

Examples of a base used in the alkansulfonylation reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic compounds such as methyllithium, ethyllithium, n-butyllithium, methylmagnesium chloride, and dimsyl sodium; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydrides such as sodium hydride, potassium hydride, and calcium hydride; and organic base compounds such as triethylamine, diisopropylethylamine, tributylamine, N,N-dimethylaniline, N,N-diethylaniline, pyridine, 4-dimethylaminopyridine, imidazole, quinoline, pyrrolidine, piperidine, collidine, lutidine, morpholine, and 1,8-diazabicyclo[5.4.0]-7-undecene.

The base may be used alone or in combination thereof. The base may be commercially available one.

An amount of the base used is preferably from 0.7 to 100 mol, more preferably from 0.8 to 50 mol, and even more preferably from 0.9 to 20 mol, per mol of a total of the isopropenyl dimethylcyclobutane compound (6C), having a hydroxymethyl group, and the isopropylidene dimethylcyclobutane compound (7C).

Examples of a solvent used in the alkanesulfonylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; and water.

The solvent may be used alone or in combination thereof. The solvent may be commercially available one.

An amount of the solvent used is preferably from 10 to 10,000 g per mol of a total of the isopropenyl dimethylcyclobutane compound (6C), having a hydroxymethyl group, and the isopropylidene dimethylcyclobutane compound (7C).

A reaction temperature in the akanesulfonylation reaction is preferably from −78 to 180° C., more preferably from −60 to 160° C., and even more preferably from −40 to 140° C.

A reaction time in the alkanesulfonylation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

The isopropenyl dimethylcyclobutane compound (6A), having an acyloxymethyl group, and the isopropylidene dimethylcyclobutane compound (7A) may be produced by subjecting the isopropenyl dimethylcyclobutane compound (6D), having alkanesulfonyloxymethyl group, and/or the isopropylidene dimethylcyclobutane compound (71) to an acyloxylation reaction with a carboxylate salt, as shown in the following chemical reaction formula (see Example 20 below).

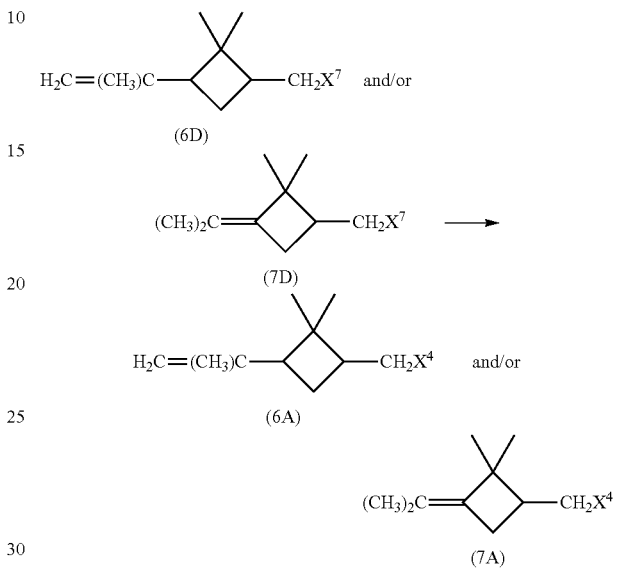

The chemical reaction formula shows the production of a mixture of the compounds (6A) and (7A) from a mixture of the compounds (6D) and (7D), the production of the compound (6A) from the compound (6D), and the production of the compound (7A) from the compound (7D).

Examples of a carboxylate salt include alkali metal salts of 3-methyl-2-butenoic acid such as lithium 3-methyl-2-butenoate, sodium 3-methyl-2-butenoate, potassium 3-methyl-2-butenoate, and cesium 3-methyl-2-butenoate; alkaline earth metal salts of 3-methyl-2-butenoic acid such as magnesium 3-methyl-2-butenoate and calcium 3-methyl-2-butenoate; and ammonium carboxylates such as ammonium 3-methyl-2-butenoate and tetrabutylammonium 3-methyl-2-butenoate.

The carboxylate salt may be used alone or in combination thereof. The carboxylate may be commercially available one.

The carboxylate salt may be prepared in a reaction system by reacting a carboxylic acid with a base such as sodium hydroxide, potassium carbonate, and tetrabutylammonium hydroxide.

An amount of the carboxylate salt used is 0.7 to 10 mol, more preferably from 0.8 to 8 mol, and even more preferably from 0.9 to 6 mol, per mol of a total of the isopropenyl dimethylcyclobutane compound (6D), having an alkanesulfonyloxymethyl group, and the isopropylidene dimethylcyclobutane compound (7D).

The acyloxylation reaction may be carried out in the presence of a halide.

Examples of a halide include metal halides such as lithium iodide, sodium iodide, potassium iodide, cesium iodide, magnesium iodide, calcium iodide, lithium bromide, sodium bromide, potassium bromide, cesium bromide, magnesium bromide, and calcium bromide; and ammonium halide compounds such as ammonium iodide, ammonium bromide, tetrabutyl ammonium iodide, tetrabutyl ammonium bromide, and tetrabutyl ammonium chloride.

The halide may be used alone or in combination thereof. The halide may be commercially available one.

An amount of the halide used is 0.0001 to 10 mol, more preferably from 0.0002 to 8 mol, and even more preferably from 0.003 to 6 mol, per mol of a total of the isopropenyl dimethylcyclobutane compound (6D), having an alkanesulfonyloxymethyl group, and the isopropylidene dimethylcyclobutane compound (7D).

Examples of a solvent used in the acyloxylation reaction include ethers such as diethyl ether, dibutyl ether, tetrahydrofuran, and 1,4-dioxane; hydrocarbons such as hexane, heptane, benzene, toluene, xylene, and cumene; chloride solvents such as methylene chloride, chloroform, and trichloroethylene; aprotic polar solvents such as N,N-dimethylformamide, 1,3-dimethyl-2-imidazolidinone, dimethyl sulfoxide, and hexamethylphosphoric triamide; nitriles such as acetonitrile and propionitrile; esters such as ethyl acetate and n-butyl acetate; alcohols such as methanol, ethanol, and t-butyl alcohol; and water.

The solvent may be used alone or in combination thereof. The solvent may be commercially available one.

An amount of the solvent used is preferably from 10 to 10,000 g per mol of a total of the isopropenyl dimethylcyclobutane compound (6D), having an alkanesulfonyloxymethyl group, and the isopropylidene dimethylcyclobutane compound (7I)).

A reaction temperature in the acyloxylation reaction is preferably from −78 to 180° C., more preferably from −60 to 160° C., and even more preferably from −40 to 140° C.

A reaction time in the acyloxylation reaction may be set arbitrarily. It is desirable in view of the yield to monitor the reaction with gas chromatography (GC) or silica gel thin layer chromatography (TLC) to confirm the completion of the reaction. A reaction time is usually about 0.5 to 24 hours.

EXAMPLES

The present invention will be further described with reference to the following Examples. It should be understood that the present invention is not limited to or by the Examples.

A sample for measuring the spectrum was obtained by purifying a crude product in some cases.

A crude yield refers to a yield of a crude product without being purified.

Example 1

Preparation of Ethyl 3-(1-ethoxycarbonylethylidene)-2,2-dimethylcyclobutanecarboxylate

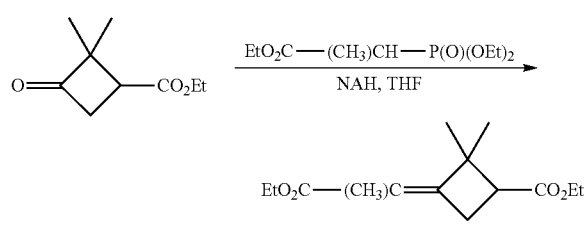

Sodium hydride (5.33 g, 0.222 mol) and tetrahydrofuran (THF) (500 g) were placed in a reactor in a nitrogen atmosphere and stirred at 10° C. to prepare a suspension. A solution of triethyl 2-phosphonopropionate (52.9 g, 0.222 mol) in THF (16 g) was added dropwise to the suspension at internal temperature in the reactor of 20° C. or below. After the completion of the dropwise addition, the suspension was stirred at 55° C. for 1 hour. Next, a solution of ethyl 2,2-dimethyl-3-oxocyclobutanecarboxylate (32.9 g, 0.193 mol) in THF (30 g) was added dropwise at internal temperature in the reactor of 60° C. or below and were stirred under reflux for 9 hours. Subsequently, water was added to the reaction mixture, and the organic layer was separated and subjected to post-treatment by ordinary washing, drying and concentration. Then, the obtained concentrated liquid was subjected to distillation at a reduced pressure to obtain the target compound, ethyl 3-(1-ethoxycarbonylethylidene)-2,2-dimethylcyclobutanecarboxylate, as a geometric isomer mixture at E:Z=57:43 (38.3 g, 0.150 mol) in a yield of 78%.

The following is spectrum data of ethyl (E)-3-(1-ethoxycarbonylethylidene)-2,2-dimethylcyclobutanecarboxylate thus produced (colorless or pale yellow oily liquid) thus produced.

IR (D-ATR): νmax=2965, 2933, 2870, 1732, 1705, 1674, 1463, 1448, 1387, 1367, 1343, 1305, 1282, 1250, 1185, 1160, 1111, 1038, 861,767 cm$^{-1}$.

$^1$H-NMR (500 MHz CDCl$_3$): δ=1.18 (3H, s), 1.22-1.28 (6H, m), 1.41 (3H, s), 1.77 (3H, t, J=2.1 Hz), 2.83 (1H, dd, J=8.0, 9.2 Hz), 3.03-3.11 (1H, m), 3.27-3.35 (1H, m), 4.10-4.21 (4H, m) ppm.

$^{13}$C-NMR (150 MHz, CDCl$_3$): δ 13.16, 14.31, 14.42, 21.11, 26.88, 30.86, 45.64, 48.25, 60.02, 60.27, 120.12, 160.91, 168 0.09, 172.82 ppm.

The following is spectrum data of ethyl (Z)-3-(1-ethoxycarbonylethylidene)-2,2-dimethylcyclobutanecarboxylate (colorless or pale yellow oily liquid) thus produced.

IR (D-ATR): νmax=2981, 2961, 2930, 2870, 1732, 1715, 1671, 1449, 1371, 1342, 1301, 1280, 1247, 1185, 1156, 1114, 1095, 1077, 1049, 860, 772 cm$^{-1}$.

$^1$H-NMR (500 MHz CDCl$_3$): δ=1.23 (3H, s), 1.26 (3H, t, J=7.3 Hz), 1.28 (3H, t, J 7.3 Hz), 1.42 (3H, s), 1.69 (3H, t, J=1.5 Hz), 2.64-2.71 (1H, m), 2.81 (1H, dd, J=7.6, 8.8 Hz), 3.01-3.08 (1H, m), 4.09-4.22 (4H, m) ppm.

$^{13}$C-NMR (150 MHz, CDCl$_3$): δ=14.19, 14.31, 14.41, 20.73, 26.59, 27.84, 44.85, 49.80, 59.99, 60.29, 120.38, 159.90, 166.68, 172.93 ppm.

Example 2

Preparation of 2-(3-hydroxymethyl-2,2-dimethylcyclobutylidene)propan-1-ol

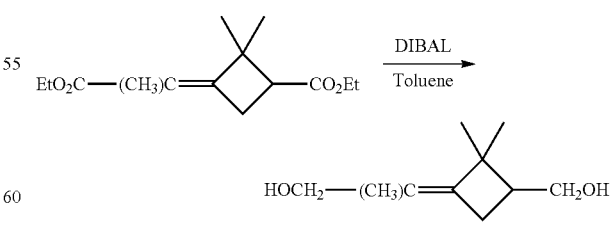

A solution of 1.01 M diisobutylaluminum hydride (DIBAL) in toluene (1 L, 1.01 mol) was placed in a reactor in a nitrogen atmosphere and stirred at −60° C. A solution of the geometric isomer mixture of E:Z=57:43 of ethyl 3-(1-ethoxycarbonylethylidene)-2,2-dimethylcyclobutanecarboxylate (36.6 g, 0.144 mol) obtained as in Example 1 in tetrahydrofuran (THF) (80 g) was added dropwise to the solution at internal temperature in the reactor of −50° C. or below. After the completion of the dropwise addition, the temperature of the mixture was gradually elevated up to 10° C., and then the mixture was stirred for 5 hours. Subsequently, a saturated aqueous solution of Rochelle salt was added to the mixture, and the organic layer was separated and subjected to post-treatment by ordinary washing, drying and concentration to obtain the target crude compound, 2-(3-hydroxymethyl-2,2-dimethylcyclobutylidene)propan-1-ol, as a geometric isomer mixture at E:Z=57:43 (24.5 g, 0.144 mol) in a crude yield of 100%.

The following is spectrum data of (E)-2-(3-hydroxymethyl-2,2-dimethylcyclobutylidene)propan-1-ol (colorless or pale yellow oily liquid) thus produced.

IR (D-ATR): vmax=3322, 2955, 2922, 2864, 1703, 1459, 1382, 1361, 1311, 1276, 1224, 1167, 1101, 1053, 1031, 1005, 942, 886 cm$^{-1}$.

$^1$H-NMR (500 MHz CDCl$_3$): δ=1.18 (3H, s), 1.28 (3H, s), 1.66 (3H, t, J=1.9 Hz), 1.76 (2H, brs), 2.06-2.13 (1H, m), 2.19-2.26 (1H, m), 2.66-2.72 (1H, m), 3.61 (1H, dd, J=7.2, 10.7 Hz), 3.75 (1H, dd, J=7.6, 10.7 Hz), 3.89 (2H, brs) ppm.

$^{13}$C-NMR (150 MHz, CDCl$_3$): δ 14.19, 20.51, 27.54, 28.24, 42.71, 44.40, 63.78, 63.88, 125.64, 142.47 ppm.

The following is spectrum data of (Z)-2-(3-hydroxymethyl-2,2-dimethylcyclobutylidene)propan-1-ol (colorless or pale yellow oily liquid) thus produced.

IR (D-ATR): vmax=3329, 2954, 2925, 2865, 1702, 1445, 1374, 1362, 1312, 1272, 1249, 1166, 1121, 1066, 1026, 1003, 888 cm$^{-1}$.

$^1$H-NMR (500 MHz CDCl$_3$): δ=1.18 (3H, s), 1.28 (3H, s), 1.56 (3H, t, J 1.3 Hz), 1.57 (2H, brs), 2.07-2.23 (2H, m), 2.59-2.65 (1H, m), 3.62 (1H, dd, J=6.8, 10.7 Hz), 3.76 (1H, dd, J=7.6, 10.7 Hz), 3.98-4.05 (2H, m) ppm.

$^{13}$C-NMR (150 MHz, CDCl$_3$): δ=15.07, 21.90, 27.63, 29.56, 42.49, 44.58, 62.51, 63.97, 126.32, 143.79 ppm.

Example 3

Preparation of [3-(2-acetoxy-1-methylethylidene)-2,2-dimethylcyclobutyl]methyl Acetate

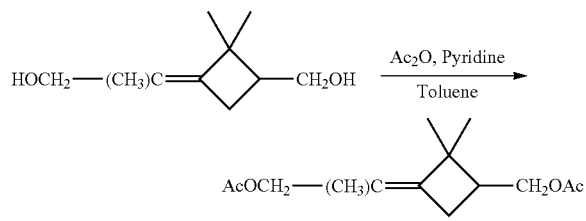

A geometric isomer mixture of E:Z 57:43 of 2-(3-hydroxymethyl-2,2-dimethylcyclobutylidene)propan-1-ol (24.5 g, 0.144 mol) obtained in Example 2, toluene (202 g), and pyridine (114 g, 1.44 mol) were placed in a reactor in a nitrogen atmosphere and stirred at 10° C. Acetic anhydride (73.6 g, 0.721 mol) was added dropwise to the solution at internal temperature in the reactor of 20° C. or below. After the completion of the dropwise addition, the mixture was stirred at 15° C. for 6 hours. Subsequently, water was added to the mixture, and the organic layer was separated and subjected to post-treatment by ordinary washing, drying and concentration. Then, the obtained concentrated liquid was subjected to distillation at a reduced pressure to obtain the target compound, [3-(2-acetoxy-1-methylethylidene)-2,2-dimethylcyclobutyl]methyl acetate, as a geometric isomer mixture at E:Z=57:43 (30.0 g, 0.118 mol) in a yield of 82%.

The following is spectrum data of [(E)-3-(2-acetoxy-1-methylethylidene)-2,2-dimethylcyclobutyl]methyl acetate (colorless or pale yellow oily liquid) thus produced.

IR (D-ATR): vmax 2958, 1740, 1459, 1380, 1365, 1235, 1171, 1023, 974, 893, 830, 605 cm$^{-1}$.

$^1$H-NMR (500 MHz CDCl$_3$): δ=1.16 (3H, s), 1.27 (3H, s), 1.61 (3H, t, J=1.9 Hz), 2.02 (3H, s), 2.04 (3H, s)), 2.20-2.29 (2H, m), 2.68-2.75 (1H, m), 4.06-4.14 (2H, m), 4.32 (1H, d, J=11.8 Hz), 4.35 (1H, d, J=11.8 Hz) ppm.

$^{13}$C-NMR (150 MHz, CDCl$_3$): δ=14.51, 20.54, 20.92, 20.95, 27.72, 27.85, 39.05, 44.62, 65.25, 65.31, 121.57, 144.58, 171.06, 171.11 ppm.

The following is spectrum data of [(Z)-3-(2-acetoxy-1-methylethylidene)-2,2-dimethylcyclobutyl]methyl acetate (colorless or pale yellow oily liquid) thus produced.

IR (D-ATR): vmax=2957, 1741, 1462, 1366, 1236, 1024, 975, 891, 631, 606 cm$^{-1}$.

$^1$H-NMR (500 MHz CDCl$_3$): δ=1.15 (3H, s), 1.26 (3H, s), 1.51-1.52 (3H, m), 2.02 (3H, s), 2.04 (3H, s), 2.17-2.27 (2H, m), 2.61-2.69 (1H, m), 4.09 (1H, d, J=5.4 Hz), 4.12 (1H, d, J 5.4 Hz), 4.47 (2H, brs) ppm.

$^{13}$C-NMR (150 MHz, CDCl$_3$): δ=15.46, 20.91, 29.94, 21.65, 27.80, 28.82, 38.88, 44.79, 64.06, 65.23, 121.91, 145.70, 171 0.05, 171.14 ppm.

Example 4

Preparation of [3-[2-(2-methylbutanoyloxy)-1-methylethylidene]-2,2-dimethylcyclobutyl]methyl 2-methylbutanoate

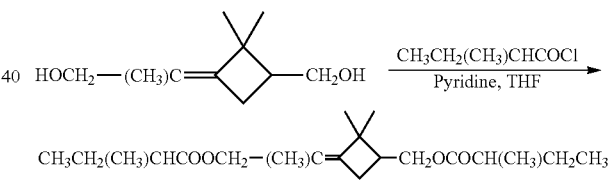

A geometric isomer mixture of E:Z=57:43 of 2-(3-hydroxymethyl-2,2-dimethylcyclobutylidene)propan-1-ol (1.72 g, 10.1 mmol) obtained as in Example 2, tetrahydrofuran (THF) (36 g), and pyridine (16 g, 0.202 mol) were placed in a reactor in a nitrogen atmosphere and stirred at 0° C. for 1 hour. 2-Methylbutanoyl chloride (4.85 g, 40.2 mmol) was added dropwise to the solution at internal temperature in the reactor of 20° C. or below. After the completion of the dropwise addition, the mixture was stirred at 20° C. for 3 hours. Subsequently, water was added to the mixture, and the organic layer was separated and subjected to post-treatment by ordinary washing, drying and concentration. Then, the obtained concentrated liquid was purified by silica gel column chromatography (hexane:ethyl acetate=30:1) to obtain the target compound, [3-[2-(2-methylbutanoyloxy)-1-methylethylidene]-2,2-dimethylcyclobutyl]methyl 2-methylbutanoate, as a geometric isomer mixture at E:Z=51:43 (1.88 g, 5.56 mmol) in a yield of 55%.

The following is spectrum data of [3-[2-(2-methylbutanoyloxy)-1-methylethylidene]-2,2-dimethylcyclobutyl]methyl 2-methylbutanoate (colorless or pale yellow oily liquid) thus produced.

$^1$H-NMR (500 MHz CDCl$_3$): δ=0.87-0.91 (6H, m), 1.12 (3H, d, J=4.2 Hz), 1.13 (3H, d, J=4.6 Hz), 1.14, 1.16 (3H, s, s), 1.26, 1.27 (3H, s, s), 1.40-1.52, 1.61-1.72 (7H, m), 2.19-2.41 (4H, m), 2.62-2.76 (1H, m), 4.08-4.27 (2H, m), 4.32-4.40, 4.44-4.50 (2H, m) ppm.

Example 5

Preparation of 1-chloromethyl-3-(2-chloro-1-methylethylidene)-2,2-dimethylcyclobutane

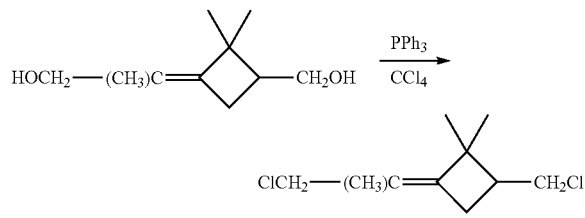

A geometric isomer mixture of E:Z=57:43 of 2-(3-hydroxymethyl-2,2-dimethylcyclobutylidene)propan-1-ol (1.64 g, 9.61 mmol) obtained as in Example 2 and carbon tetrachloride (48 g, 0.31 mol) were placed in a reactor in a nitrogen atmosphere and stirred at 0° C. Subsequently, triphenylphosphine (7.56 g, 28.8 mmol) was added, and the mixture was stirred for 24 hours, while heated gradually to a temperature of 20° C. Subsequently, methanol (5 g) was added to the reaction mixture at an ambient temperature, and stirred for 1 hour. The reaction mixture was concentrated, followed by addition of hexane and removal of the precipitate by filtration. The filtrate was concentrated, and the concentrate was purified by silica gel column chromatography (hexane) to obtain the target compound, 1-chloromethyl-3-(2-chloro-1-methylethylidene)-2,2-dimethylyclobutane, as a geometric isomer mixture at E:Z=57:43 (1.06 g, 5.13 mmol) in a yield of 53%.

The following is spectrum data of 1-chloromethyl-3-(2-chlor-1-methylethylidene)-2,2-dimethylyclobutane (colorless or pale yellow oily liquid) thus produced.

$^1$H-NMR (500 MHz CDCl$_3$): δ=1.20, 1.23 (3H, s), 1.31, 1.35 (3H, s), 1.59, 1.71 (3H, m), 2.21-2.37 (2H, m), 2.70-2.85 (1H, m), 3.50-3.54 (1H, m), 3.61-3.66 (1H, m), 3.89, 4.02 (2H, m) ppm.

Example 6

Preparation of [2-(3-hydroxymethyl-2,2-dimethylcyclobutylidene)propyl]triphenylphosphonium Bromide

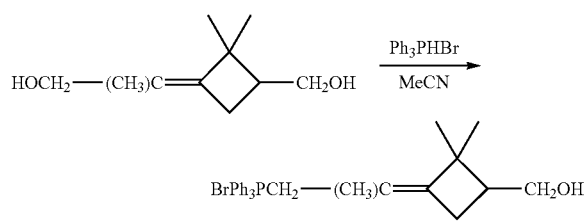

A geometric isomer mixture of E:Z=57:43 of 2-(3-hydroxymethyl-2,2-dimethylcyclobutylidene)propan-1-ol (300 mg, 1.76 mmol) obtained as in Example 2, acetonitrile (12 g), and triphenylphosphine hydrobromide (670 mg, 1.95 mmol) were placed in a reactor in a nitrogen atmosphere and stirred under reflux for 5 hours. Pyridine (1 g) was added to a solution of the obtained [2-(3-hydroxymethyl-2,2-dimethylcyclobutylidene)propyl]triphenylphosphonium bromide, and the mixture was concentrated at a reduced pressure. Next, toluene (12 g) was added to the concentrated solution, and concentration at a reduced pressure was carried out twice to obtain the target crude compound, [2-(3-hydroxymethyl-2,2-dimethylcyclobutylidene)propyl]triphenylphosphonium bromide, (872 mg, 1.76 mmol) in a crude yield of 100%.

The following is spectrum data of [2-(3-hydroxymethyl-2,2-dimethylcyclobutylidene)propyl]triphenylphosphonium bromide (colorless or pale yellow oily liquid) thus produced.

$^1$H-NMR (500 MHz CD$_3$CN): δ=0.72, 1.06 (3H, a), 0.85, 1.17 (3H, s), 1.28-1.32, 1.43-1.47 (3H, m), 1.47-2.70 (3H, m), 3.18-3.22, 3.32-3.46 (2H, m), 3.83, 3.91 (2H, d, J=14.6 Hz, d, J 14.6 Hz), 7.26-7.92 (15H, m) ppm.

Example 7

Preparation of [2,2-dimethyl-3-(2-bromo-1-methylethylidene)cyclobutyl]methyl Acetate

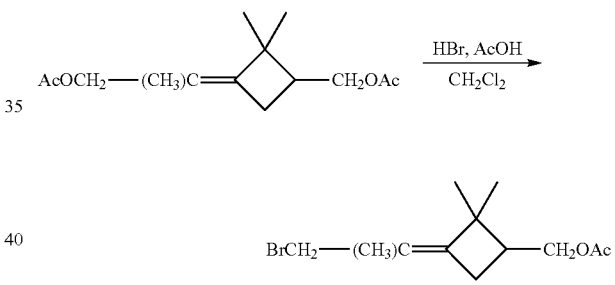

A geometric isomer mixture of E:Z=57:43 of [3-(2-acetoxy-1-methylethylidene)-2,2-dimethylcyclobutyl] methyl acetate (1.78 g, 6.99 mmol) obtained in Example 3, methylene chloride (30 g) and a 30% solution of hydrogen bromide in acetic acid (2.83 g, 10.5 mmol) were placed in a reactor in a nitrogen atmosphere and stirred at 20° C. for 6 hours. Subsequently, a saturated aqueous solution of sodium bicarbonate was added to the reaction mixture, and the organic layer was separated and subjected to post-treatment by ordinary washing, drying, and concentration. Then, the obtained concentrated liquid was purified by silica gel column chromatography (hexane:ethyl acetate=30:1) to obtain the target 6 compound, [2,2-dimethyl-3-(2-bromo-1-methylethylidene)cyclobutyl]methyl acetate, as a geometric isomer mixture at E:Z=57:43 (1.70 g, 6.18 nmol) in a yield of 88%.

The following is spectrum data of [2,2-dimethyl-3-(2-bromo-1-methylethylidene)cyclobutyl]methyl acetate (colorless or pale yellow oily liquid) thus produced.

$^1$H-NMR (500 MHz CDCl$_3$): δ=1.15, 1.20 (3H, s, s), 1.26 1.31 (3H, s, s), 1.59-1.60, 1.70-171 (3H, m), 2.03 (3H, s), 2.15-2.29 (2H, m), 2.60-2.75 (1H, m), 3.82, 3.94, 3.97 (2H, s, d, J=9.6 Hz, d, J 9.6 Hz), 4.08-4.15 (2H, m) ppm.

Example 8

Preparation of (3-isopropenyl-2,2-dimethylcyclobutyl)methyl acetate and (3-isopropylidene-2,2-dimethylcyclobutyl)methylacetate

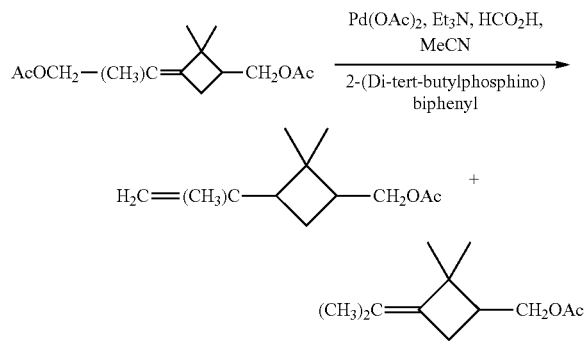

A geometric isomer mixture of E:Z=57:43 of [3-(2-acetoxy-1-methylethylidene)-2,2-dimethylcyclobutyl]methyl acetate (483 mg, 1.90 mmol) obtained in Example 3, acetonitrile (12 g), 2-(di-tert-butylphosphino)biphenyl (230 mg, 0.771 mmol), and palladium acetate (40 mg, 0.18 mmol) were placed in a reactor in a nitrogen atmosphere and stirred at 20° C. Then, triethylamine (770 mg, 7.61 mmol) and formic acid (260 mg, 5.65 mmol) were added to form triethylammonium formate in the reaction system, and stirred at 30° C. for 19 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=50:1) to obtain the target compounds, (3-isopropenyl-2,2-dimethylcyclobutyl)methyl acetate and (3-isopropylidene-2,2-dimethylcyclobutyl)methyl acetate, as a mixture of 78:18:4 of the cis form, the trans form and the regioisomer at the double bond (i.e., (3-isopropylidene-2,2-dimethylcyclobutyl)methyl acetate), (328 mg, 1.67 mmol) in a yield of 88%.

The following is spectrum data of cis-(3-isopropenyl-2,2-dimethylcyclobutyl)methyl acetate (colorless or pale yellow oily 16 liquid) thus produced.

IR (D-ATR): νmax=3080, 2957, 2870, 1743, 1647, 1460, 1385, 1368, 1240, 1162, 1031, 972, 886, 641, 607, 556 cm$^{-1}$.

$^1$H-NMR (500 MHz CDCl$_3$): δ=0.81 (3H, s), 1.19 (3H, s), 1.59 (1H, q, J=10.7 Hz) 1.64 (3H, t, J=0.8 Hz), 1.89 (1H, dt, J=7.6, 10.7 Hz), 2.02 (3H, s), 2.13-2.22 (1H, m), 2.37-2.41 (1H, m) 3.94 (1H, dd, J=8.6, 11.3 Hz); 4.04 (1H, dd, J=6.3, 11.3 Hz); 4.56 (1H, brs); 4.79-4.82 (1H, m) ppm.

$^{13}$C-NMR (150 MHz, CDCl$_3$): δ=16.07, 21.02, 22.92, 22.96, 30.92, 39.74, 41.05, 48.83, 64.95, 109.42, 144.93, 171.05 ppm.

Example 9

Preparation of (3-isopropenyl-2,2-dimethylcyclobutyl)methyl Acetate and (3-isopropylidene-2,2-dimethylcyclobutyl)methyl Acetate

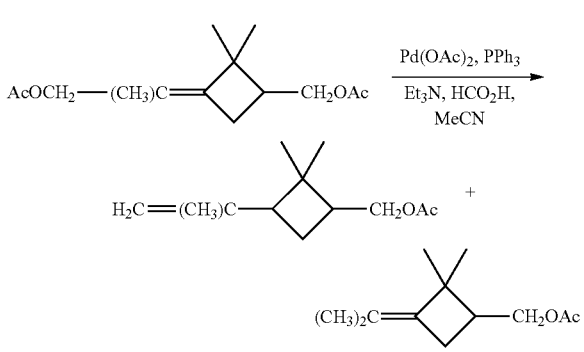

A geometric isomer mixture of E:Z 57:43 of [3-(2-acetoxy-1-methylethylidene)-2,2-dimethylcyclobutyl]methyl acetate (483 mg, 1.90 mmol) obtained in Example 3, acetonitrile (12 g), triphenylphosphine (200 mg, 0.763 mmol), and palladium acetate (40 mg, 0.18 mmol) were placed in a reactor in a nitrogen atmosphere and stirred at 20° C. Then, triethylamine (770 mg, 7.61 mmol) and formic acid (260 mg, 5.65 mmol) were added to form triethylammonium formate in the reaction system, and stirred under reflux for 24 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=50:1) to obtain the target compounds, (3-isopropenyl-2,2-dimethylcyclobutyl)methyl acetate and (3-isopropylidene-2,2-dimethylcyclobutyl)ethyl acetate, as a mixture of 68:30:2 of the cis form, the trans form, and the regioisomer at the double bond (i.e., (3-isopropylidene-2,2-dimethylcyclobutyl)methyl acetate), (321 mg, 1.63 mmol) in a yield of 86%.

Example 10

Preparation of (3-isopropenyl-2,2-dimethylcyclobutyl)methyl Acetate and (3-isopropylidene-2,2-dimethylcyclobutyl)methylacetate

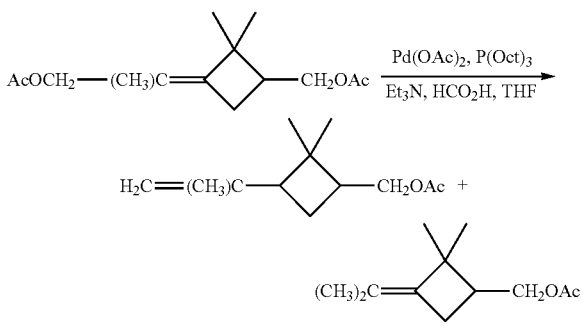

A geometric isomer mixture of E:Z=57:43 of [3-(2-acetoxy-1-methylethylidene)-2,2-dimethylcyclobutyl]methyl acetate (1.86 g, 7.33 mmol) obtained in Example 3, tetrahydrofuran (THF) (19 g), trioctylphosphine (220 mg, 0.594 nmol), and palladium acetate (33 mg, 0.15 mmol) were placed in a reactor in a nitrogen atmosphere and stirred at 20° C. Then, triethylamine (2.97 g, 29.3 mmol) and formic acid (1.01 g, 22.0 mmol) were added to form triethylammonium formate in the reaction system, and stirred at 35° C. for 5 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=50:1) to obtain the target compounds, (3-isopropenyl-2,2-dimethylcyclobutyl)methyl acetate and (3-isopropylidene-2,2-dimethylcyclobutyl)methy acetate, as a mixture of 65:34:1 of the cis form, the trans form, and the regioisomer at the double bond (i.e., (3-isopropylidene-2,2-dimethylcyclobutyl)methyl acetate), (1.27 g, 6.45 mmol) in a yield of 88%.

stirred at 45° C. for 4 hours. Then, acetic acid and brine were added to the reaction mixture, and the organic layer was separated and subjected to post-treatment by ordinary washing, drying and concentration. Then, the obtained concentrated liquid was subjected to distillation at a reduced pressure to obtain the target compounds, (3-isopropenyl-2,2-dimethylcyclobutyl)methyl acetate and (3-isopropylidene-2,2-dimethylcyclobutyl)methyl acetate, as a mixture of 68:31:1 of the cis form, the trans form, and the regioisomer at the double bond (i.e., (3-isopropylidene-2,2-dimethylcyclobutyl)methyl acetate), (310 g, 1.58 mmol) in a yield of 96%. The spectrum data of cis-(3-isopropenyl-2,2-dimethylcyclobutyl)methyl acetate thus obtained (colorless or pale yellow oily liquid) had the same spectra as in Example 8.

Example 12

Preparation of (3-isopropenyl-2,2-dimethylcyclobutyl)methyl 2-methylbutanoate and (3-isopropylidene-2,2-dimethylcyclobutyl)methyl 2-methylbutanoate

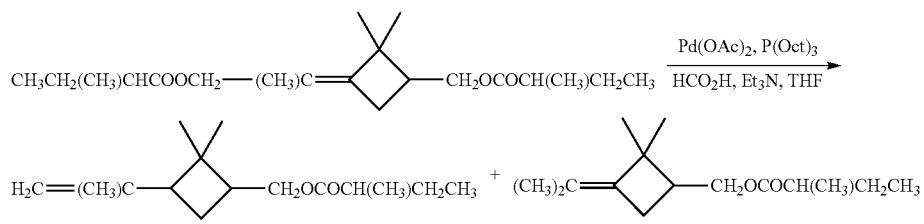

Example 11

Preparation of (3-isopropenyl-2,2-dimethylcyclobutyl)methyl acetate and (3-isopropylidene-2,2-dimethylcyclobutyl)methylacetate

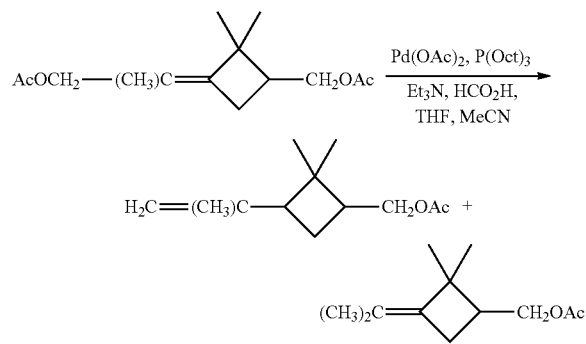

Palladium acetate (1.86 g, 8.27 mmol), tetrahydrofuran (THF) (1602 g), trioctylphosphine (12.3 g, 33.1 mmol), and [3-(2-acetoxy-1-methylethylidene)-2,2-dimethylcyclobutyl] methyl acetate as a geometric isomer mixture at E:Z=70:30 (420 g, 1.65 mol) were placed in a reactor in a nitrogen atmosphere and stirred at 45° C. Subsequently, a solution of triethylamine (335 g, 3.31 mol) and formic acid (114 g, 2.48 mol) in acetonitrile (MeCN) (335 g) was added dropwise at internal temperature in the reactor of 50° C. or below. After the completion of the dropwise addition, the mixture was A geometric isomer mixture of E:Z 57:43 of (3-[2-(2-methylbutanoyloxy)-1-methylethylidene]-2,2-dimethylcyclobutyl)methyl 2-methylbutanoate (1.84 g, 5.43 mmol) obtained in Example 4, tetrahydrofuran (THF) (40 g), trioctylphosphine (160 mg, 0.436 mmol), and palladium acetate (24 mg, 0.11 mmol) were placed in a reactor in a nitrogen atmosphere and stirred at 20° C. for 1 hour. Then, triethylamine (2.19 g, 21.7 nmol) and formic acid (750 mg, 16.3 mmol) were added to form triethylammonium formate in the reaction system, and stirred at 35° C. for 24 hours. Subsequently, water was added to the reaction mixture, and the organic layer was separated and subjected to post-treatment by ordinary washing drying and concentration. Then, the obtained concentrated liquid was purified by silica gel column chromatography (hexane:ethyl acetate 80:1) to obtain the target compounds, (3-isopropenyl-2,2-dimethylcyclobutyl)methyl 2-methylbutanoate and (3-isopropylidene-2,2-dimethylcyclobutyl)methyl 2-methylbutanoate, as a mixture of 64:32:4 of the cis form, the trans form, and the regioisomer at the double bond (i.e., (3-isopropylidene-2,2-dimethylcyclobutyl)methyl 2-methylbutanoate), (1.15 g, 4.84 mmol) in a yield of 89%.

The following is spectrum data of cis-(3-isopropenyl-2,2-dimethylcyclobutyl)methyl 2-methylbutanoate (colorless or pale yellow oily liquid) thus produced.

$^1$H-NMR (500 MHz CDCl$_3$): δ=0.81 (3H, s), 0.89 (3H, t, J=7.5 Hz), 1.11 (3H, q, J=7.0 Hz), 1.20 (3H, s), 1.40-1.51 (1H, m), 1.56-1.72 (5H, m), 1.87 (1H, dt, J=7.6, 10.7 Hz), 2.13-2.22 (1H, m), 2.29-2.41 (2H, m), 3.92, 3.94 (1H, dd, J=6.1, 11.1 Hz, dd, J=6.1, 11.1 Hz, 4.04, 4.05 (1H, dd, J=6.1, 11.1 Hz, dd, J=6.1, 11.1 Hz), 4.55 (1H, brs), 4.78-4.81 (1H, m) ppm.

Example 13

Preparation of 1-chloromethyl-3-isopropenyl-2,2-dimethylcyclobutane and 1-chloromethyl-3-isopropylidene-2,2-dimethylcyclobutane

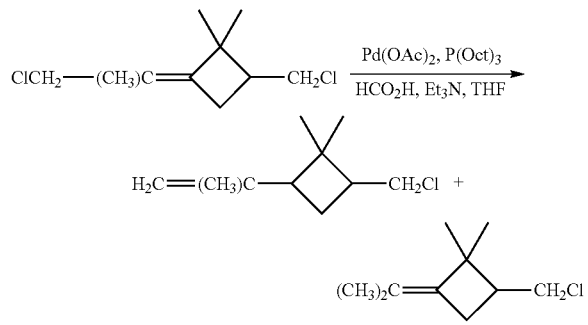

A geometric isomer mixture of E:Z=57:43 of 1-chloromethyl-3-(2-chloro-1-methylethylidene)-2,2-dimethylcyclobutane (988 mg, 4.77 mol) obtained in Example 5, tetrahydrofuran (THF) (20 g), trioctylphosphine (280 mg, 0.763 mmol), and palladium acetate (40 mg, 0.18 mmol) were placed in a reactor in a nitrogen atmosphere and stirred at 20° C. for 1 hour. Then, triethylamine (1.93 g, 19.1 nmol) and formic acid (660 mg, 14.3 mmol) were added to form triethylammonium formate in the reaction system, and stirred at 55° C. for 24 hours. Subsequently, water was added to the reaction mixture, and the organic layer was separated and subjected to post-treatment by ordinary washing, drying and concentration. Then, the obtained concentrated liquid was purified by silica gel column chromatography (hexane) to obtain the target compounds, 1-chloromethyl-3-isopropenyl-2,2-dimethylcyclobutane and 1-chloromethyl-3-isopropylidene-2,2-dimethylcyclobutane, as a mixture of 53:46:1 of the cis form, the trans form, and the regioisomer at the double bond (i.e., 1-chloromethyl-3-isopropylidene-2,2-dimethylcyclobutane), (553 mg, 3.20 mmol) in a yield of 67%.

The following is spectrum data of 1-chloromethyl-3-isopropenyl-2,2-dimethylcyclobutane (colorless or pale yellow oily liquid) thus produced.

$^1$H-NMR (500 MHz CDCl$_3$): δ=0.85, 0.98 (3H, s), 1.14, 1.26 (3H, s), 1.57, 1.72 (1H, q, J=10.7 Hz, m), 1.66-1.67 (3H, m), 1.98, 2.04-2.10 (1H, dt, J=7.7, 10.7 Hz, m), 2.15-2.30 (1H, m), 2.35-2.39, 2.52-2.57 (1H, m), 3.40-3.49, 3.60, 3.72 (2H, m, dd, J=8.8, 10.7 Hz, dd, J=6.8, 10.7 Hz), 4.56, 4.66 (1H, brs, brs), 4.80-4.83, 4.85-4.87 (1H, m) ppm.

Example 14

Preparation of (3-isopropenyl-2,2-dimethylcyclobutyl)methanol

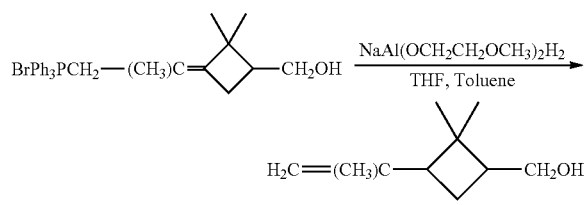

The target crude product, [2-(3-Hydroxymethyl-2,2-dimethylcyclobutylidene)propyl]triphenylphosphonium bromide, (872 mg, 1.76 mmol) obtained in Example 6 and tetrahydrofuran (THF) (70 g) were placed in a reactor in a nitrogen atmosphere and stirred at 0° C. Subsequently, a solution of 3.60 M sodium bis(2-methoxyethoxy) aluminum hydride (2.00 ml, 7.20 mmol) in toluene was added dropwise at internal temperature in the reactor of 10° C. or below. After the completion of the dropwise addition, the mixture was heated gradually up to 20° C. with stirring for 1 hour. Subsequently, a 10% by weight solution of sodium hydroxide in water was added to the reaction mixture, and the organic layer was separated and subjected to post-treatment by ordinary washing, drying and concentration. Then, the obtained concentrated liquid was purified by silica gel column chromatography (hexane:ethyl acetate=10:1) to obtain the target compound, (3-isopropenyl-2,2-dimethylcyclobutyl)methanol, as a geometric isomer mixture at 77:23 of the cis form and the trans form, (195 mg, 1.27 mmol) in a yield of 72%. Double bond regioisomer, (3-isopropylidene-2,2-dimethylcyclobutyl)methanol was not detected in GC.

The following is spectrum data of cis-(3-isopropenyl-2,2-dimethylcyclobutyl)methanol (colorless or pale yellow oily liquid) thus produced.

$^1$H-NMR (500 MHz CDCl$_3$): δ=0.82 (3H, s), 1.22 (3H, s), 1.55 (1H, q, J=10.7 Hz), 1.65 (3H, s), 1.85-1.91 (1H, m), 2.03-2.10 (1H, m), 2.34-2.39 (1H, m), 3.52 (1H, dd, J=6.5, 10.7 Hz), 3.59 (1H, dd, J=8.3, 10.7 Hz), 4.55 (1H, brs), 4.78-4.81 (1H, m) ppm.

The following is spectrum data of trans-(3-isopropenyl-2,2-dimethylcyclobutyl)methanol (colorless or pale yellow oily liquid) thus produced.

$^1$H-NMR (500 MHz CDCl$_3$): δ=0.95 (3H, s), 1.12 (3H, s), 1.51 (1H, brs), 1.58-1.63 (1H, m), 1.65 (3H, s), 1.76-1.90 (1H, m), 2.03-2.14 (1H, m), 2.53-2.59 (1H, m), 3.69 (1H, dd, J=7.6, 10.7 Hz), 3.85 (1H, dd, J=7.3, 10.7 Hz), 4.62 (1H, brs), 4.81-4.84 (1H, m) ppm.

Example 15

Preparation of (3-isopropylidene-2,2-dimethylcyclobutyl)methanol

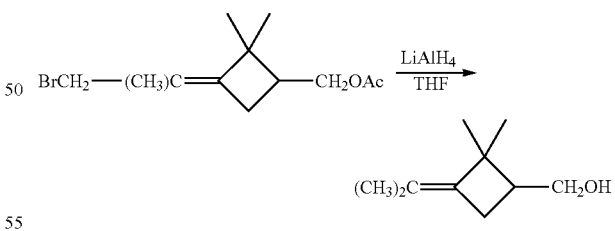

Lithium aluminum hydride (570 mg, 15.0 mmol) and tetrahydrofuran (THF) (60 g) were placed in a reactor in a nitrogen atmosphere and stirred at 0° C. for 1 hour. A geometric isomer mixture of E:Z=57:43 of [2,2-dimethyl-3-(2-bromo-1-methylethylidene)cyclobutyl]methyl acetate (1.62 g, 5.89 mmol) was added dropwise to this solution at internal temperature in the reactor of 5° C. or below. After the completion of the dropwise addition, the mixture was heated gradually up to 20° C. for 6 hour with stirring. Subsequently, water (570 mg) and a 15% by weight solution of sodium hydroxide (570 mg) were added, followed by further addition of water (1.71 g), and filtration. The obtained filtrate was concentrated at a reduced pressure, and purified by silica gel column chromatography (hexane:ethyl acetate=10:1) to obtain the target compound, (3-isopropylidene-2,2-dimethylcyclobutyl)methanol (909 mg, 5.89 mmol) in a yield of 100%.

Double bond regioisomer, (3-isopropenyl-2,2-dimethylcyclobutyl)methanol was not detected in GC.

The following is spectrum data of (3-isopropylidene-2,2-dimethylcyclobutyl)methanol (colorless or pale yellow oily liquid) thus produced.

$^1$H-NMR (500 MHz CDCl$_3$): δ=1.15 (3H, s), 1.26 (3H, s), 1.45 (3H, s), 1.56-1.58 (3H, m), 1.63 (1H, brs), 2.03-2.14 (2H, m), 2.54-2.62 (1H, m), 3.61 (1H, dd, J=6.9, 10.7 Hz), 3.76 (1H, dd, J=7.7, 10.7 Hz) ppm.

$^{13}$C-NMR (150 MHz, CDCl$_3$): δ=18.48, 19.53, 20.90, 27.70, 28.67, 42.65, 44.05, 64.30, 122.42, 137.39 ppm.

Example 16

Preparation of (3-isopropenyl-2,2-dimethylcyclobutyl)methyl acetate and (3-isopropylidene-2,2-dimethylcyclobutyl)methylacetate

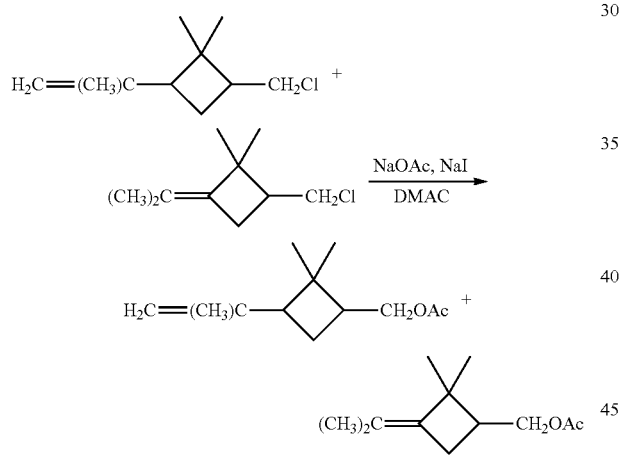

A mixture of 1-chloromethyl-3-isopropenyl-2,2-dimethylcyclobutane and 1-chloromethyl-3-isopropylidene-2,2-dimethylcyclobutane (535 mg, 3.10 mmol) obtained as in Example 13, sodium acetate (580 mg, 7.07 mmol), sodium iodide (100 mg, 0.667 mmol), and N,N-dimethylacetamide (20 g) were placed in a reactor in a nitrogen atmosphere and stirred at 150° C. for 24 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate:=50:1) to obtain the target compounds, (3-isopropenyl-2,2-dimethylcyclobutyl)methyl acetate and (3-isopropylidene-2,2-dimethylcyclobutyl) methyl acetate, as a mixture of 57:42:1 of the cis form, the trans form, and the regioisomer at the double bond (i.e., (3-isopropylidene-2,2-dimethylcyclobutyl)methyl acetate), (255 mg, 1.30 mmol) in a yield of 42%.

Example 17

Preparation of (3-isopropenyl-2,2-dimethylcyclobutyl)methyl acetate

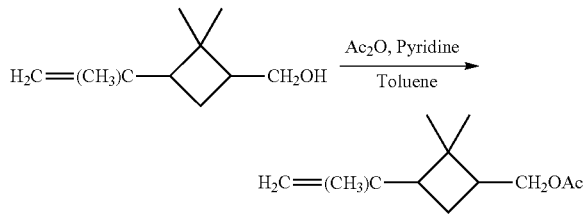

A geometric isomer mixture of 77:23 of the cis form and the trans form of (3-isopropenyl-2,2-dimethylcyclobutyl) methano obtained as in Example 14 (154 mg, 1.00 mmol), pyridine (316 mg) and toluene (10 g) were placed in a reactor in a nitrogen atmosphere and stirred at 0° C. Subsequently, acetic anhydride (204 mg, 2.00 mmol) was added dropwise at internal temperature in the reactor of 10° C. or below. After the completion of the dropwise addition, the mixture was heated gradually up to 20° C. for 6 hours with stirring. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropenyl-2,2-dimethylcyclobutyl)methyl acetate, as a geometric isomer mixture at 77:23 of the cis form and the trans form, (183 mg, 0.930 mmol) in a yield of 93%.

Example 18

Preparation of (3-isopropylidene-2,2-dimethylcyclobutyl)methyl Acetate

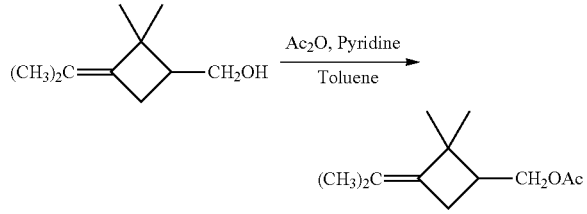

(3-isopropylidene-2,2-dimethylcyclobutyl)methanol (818 mg, 5.30 mmol) obtained as in Example 15, toluene (10 g), pyridine (1.68 g, 21.2 mmol) and acetic anhydride (1.09 g, 10.7 mmol) were placed in a reactor in a nitrogen atmosphere and stirred at 20° C. for 24 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate 50:1) to obtain the target compound, (3-isopropylidene-2,2-dimethylcyclobutyl)methyl acetate, (911 mg, 4.64 mmol) in a yield of 88%.

The following is spectrum data of (3-isopropylidene-2,2-dimethylcyclobutyl)methyl acetate (colorless or pale yellow oily liquid) thus produced.

$^1$H-NMR (500 MHz CDCl$_3$): δ=1.13 (3H, s), 1.24 (3H, s), 1.45 (3H, s), 1.57 (3H, t, J=1.9 Hz), 2.03 (3H, s), 2.10-2.22 (2H, m), 2.56-2.63 (1H, m), 4.07-4.15 (2H, m) ppm.

$^{13}$C-NMR (150 MHz, CDCl$_3$): δ=18.49, 19.53, 20.98, 21.00, 27.72, 28.37, 38.99, 44.20, 65.73, 122.67, 136.93, 171.20 ppm.

Example 19

Preparation of (3-isopropylidene-2,2-dimethylcyclobutyl)methyl methanesulfonate

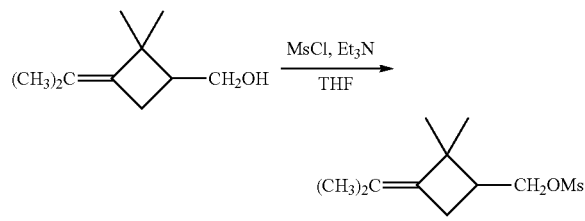

(3-Isopropylidene-2,2-dimethylcyclobutyl)methanol (858 mg, 5.56 mmol) obtained according to Example 15, tetrahydrofuran (THF) (20 g), and triethylamine (1.71 g, 16.9 mmol) were placed in a reactor in a nitrogen atmosphere and stirred at 0° C. for 1 hour. Methanesulfonyl chloride (1.09 g, 10.7 mmol) was added dropwise to this solution at internal temperature in the reactor of 10° C. or below. After the completion of the dropwise addition, the mixture was stirred at 20° C. for 1 hour. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=10:1) to obtain the target compound, (3-isopropylidene-2,2-dimethylcyclobutyl)methyl methanesulfonate, (1.29 g, 5.56 mol) in a yield of 100%.

The following is spectrum data of (3-isopropylidene-2,2-dimethylcyclobutyl)methyl methanesulfonate (colorless or pale yellow oily liquid) thus produced.

$^1$H-NMR (500 MHz CDCl$_3$): δ=1.17 (3H, s), 1.27 (3H, s), 1.45 (3H, brs), 1.58 (3H, t, J 1.9 Hz), 2.15-2.22 (1H, m), 2.25-2.33 (1H, m), 2.61-2.67 (1H, m), 3.00 (3H, s), 4.23 (1H, dd, J=7.3, 9.9 Hz), 4.31 (1H, dd, J=8.0, 10.01 Hz) ppm.

Example 20

Preparation of (3-isopropylidene-2,2-dimethylcyclobutyl)methyl 3-methyl-2-butenoate

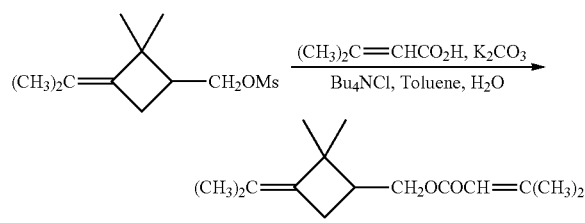

(3-Isopropylidene-2,2-dimethylcyclobutyl)methyl methanesulfonate (1.29 g, 5.56 mmol) obtained as in Example 19, toluene (40 g), water (430 mg), senecioic acid (3-methyl-2-butenoic acid) (690 mg, 6.92 mmol), potassium carbonate (610 mg, 4.39 mmol), and tetrabutylammonium chloride (60 mg, 0.23 mmol) were placed in a reactor in a nitrogen atmosphere and stirred at 100° C. for 24 hours. Subsequently, water was added to the reaction mixture, and the organic layer was separated and subjected to post-treatment by ordinary washing, drying and concentration. Then, the obtained concentrated liquid was purified by silica gel column chromatography (hexane:ethyl acetate=50:1) to obtain the target compound, (3-isopropylidene-2,2-dimethylcyclobutyl)methyl 3-methyl-2-butenoate, (1.20 g, 5.06 mmol) in a yield of 91%.

The following is spectrum data of (3-isopropylidene-2,2-dimethylcyclobutyl)methyl 3-methyl-2-butenoate (colorless or pale yellow oily liquid) thus produced.

IR (D-ATR): νmax=2956, 2917, 2864, 1719, 1659, 1449, 1376, 1361, 1349, 1272, 1227, 1146, 1076, 993, 851 cm$^{-1}$.

$^1$H-NMR (500 MHz, CDCl$_3$): δ=1.14 (3H, s), 1.25 (3H, s), 1.45 (3H, brs), 1.56-1.58 (3H, m), 1.88 (3H, d, J=1.5 Hz), 2.12-2.30 (5H, m), 2.56-2.64 (1H, m), 4.11 (1H, dd, J=6.8, 11.4 Hz), 4.15 (1H, dd, J=8.0, 11.5 Hz), 5.64-5.66 (1H, m) ppm.

$^{13}$C-NMR (150 MHz, CDCl$_3$): δ=18.50, 19.54, 20.15, 20.99, 27.34, 27.78, 28.39, 39.14, 44.21, 64.75, 116.15, 122.53, 137.18, 156.25, 166.82 ppm.

Example 21

Preparation of (3-isopropenyl-2,2-dimethylcyclobutyl)methanol and (3-isopropylidene-2,2-dimethylcyclobutyl)methanol

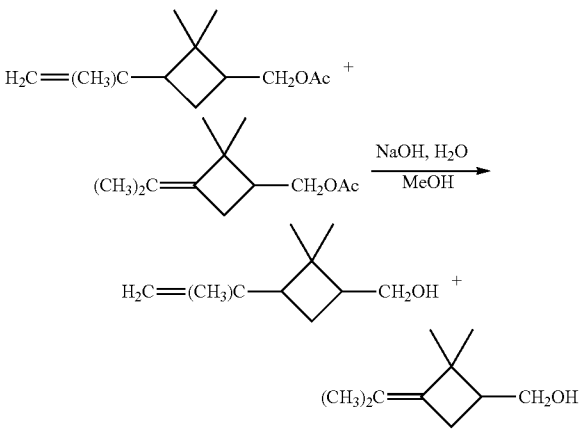

A geometric isomer mixture of (3-isopropenyl-2,2-dimethylcyclobutyl)methyl acetate (60.3 g, 307 mmol) obtained as in Example 11, methanol (94 g), and a 25% aqueous solution of sodium hydroxide (94 g) were placed in a reactor in a nitrogen atmosphere and stirred at 20° C. for 12 hours. Subsequently, brine was added to the reaction mixture, and the organic layer was separated and subjected to post-treatment by ordinary washing, drying and concentration. Then, the obtained concentrated liquid was subjected to distillation at a reduced pressure to obtain the target compounds, (3-isopropenyl-2,2-dimethylcyclobutyl)methanol and (3-isopropylidene-2,2-dimethylcyclobutyl)methanol, as a mixture of 67:32:1 of the cis form, the trans form, and the regioisomer at the double bond (i.e., (3-isopropylidene-2,2-dimethylcyclobutyl)methanol), (46.0 g, 298 mmol) in a yield of 97%. The spectra data of cis-(3-isopropenyl-2,2-dimethylcyclobutyl)methanol thus obtained (colorless or pale yellow oily liquid) and trans-(3-isopropenyl-2,2-dimethylcyclobutyl)methanol thus obtained (colorless or pale yellow oily liquid) had the same spectra as in Example 14.

Example 22

Preparation of (3-isopropenyl-2,2-dimethylcyclobutyl)methyl 2-methylbutanoate and (3-isopropylidene-2,2-dimethylcyclobutyl)methyl 2-methylbutanoate

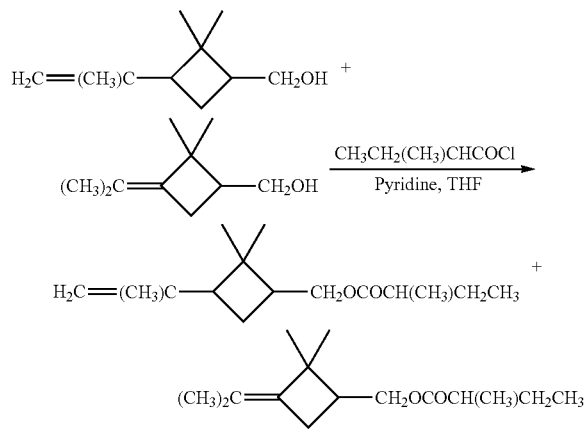

A geometric isomer mixture of (3-isopropenyl-2,2-dimethylcyclobutyl)methanol (12.6 g, 82.0 mmol) obtained as in Example 21, tetrahydrofuran (TH) (100 g), and pyridine (16.9 g, 213 mmol) were placed in a reactor in a nitrogen atmosphere and stirred at 0° C. Subsequently, 2-methylbutanoyl chloride (12.9 g, 107 mmol) was added dropwise to the solution at internal temperature in the reactor of 15° C. or below. After the completion of the dropwise addition, the mixture was heated gradually up to 20° C. for 6 hours with stirring. Subsequently, brine was added to the reaction mixture, and the organic layer 16 was separated and subjected to post-treatment by ordinary washing, drying and concentration. Then, the obtained concentrated liquid was subjected to distillation at a reduced pressure to obtain the target compounds, (3-isopropenyl-2,2-dimethylcyclobutyl)methyl 2-methylbutanoate and (3-isopropylidene-2,2-dimethylcyclobutyl)methyl 2-methylbutanoate, as a mixture of 68:31:1 of the cis form, the trans form, and the regioisomer at the double bond (i.e., (3-isopropylidene-2,2-dimethylcyclobutyl)methyl 2-methylbutanoate), (19.5 g, 81.6 mmol) in a yield of 100%. The spectra data of cis-(3-isopropenyl-2,2-dimethylcyclobutyl)methyl 2-methylbutanoate thus obtained ad the same spectra as in Example 14.

Example 23

Preparation of (3-isopropenyl-2,2-dimethylcyclobutyl)methyl 3-methyl-3-butenoate and (3-isopropylidene-2,2-dimethylcyclobutyl)methyl 3-methyl-3-butenoate

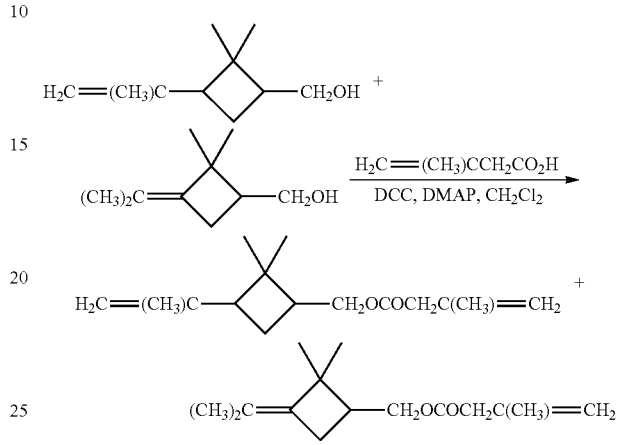

A geometric isomer mixture of (3-isopropenyl-2,2-dimethylcyclobutyl)methanol (13.4 g, 86.6 mmol) obtained as in Example 21, dichloromethane (665 g), 3-methyl-3-butenoic acid (12.5 g, 125 mmol), and 4-dimethylaminopyridine (DMAP)(1.06 g, 8.66 mmol) were placed in a reactor in a nitrogen atmosphere and stirred at 0° C. N,N'-dicyclohexylcarbodiimide (DCC) (24.8 g, 120 mmol) was added. The mixture was heated gradually up to 20° C. for 2 hours with stirring. Subsequently, ether and brine were added to the reaction mixture, and the organic layer was separated and subjected to post-treatment by ordinary washing, drying and concentration. Then, the obtained concentrated liquid was purified by silica gel column chromatography (hexane:ethyl acetate=40:1) to obtain the target compounds, (3-isopropenyl-2,2-dimethylcyclobutyl)methyl 3-methyl-3-butenoate and (3-isopropylidene-2,2-dimethylcyclobutyl)methyl 3-methyl-3-butenoate, as a mixture of 67:32:1 of the cis form, the trans form, and the regioisomer at the double bond (i.e., (3-isopropylidene-2,2-dimethylcyclobutyl)methyl 3-methyl-3-butenoate), (20.2 g, 85.6 nmol) in a yield of 99%.

The following is spectrum data of cis-(3-isopropenyl-2,2-dimethylcyclobutyl)methyl 3-methyl-3-butenoate (colorless or pale yellow oily liquid) thus produced.

IR (D-ATR): νmax=3080, 2956, 2870, 1738, 1648, 1454, 1385, 1370, 1337, 1284, 1241, 1153, 1075, 1030, 994, 889 cm-1.

$^1$H-NMR (500 MHz CDCl$_3$): δ=0.80 (3H, s), 1.19 (3H, s), 1.61 (1H, q, J 10.7 Hz), 1.64-1.65 (3H, m), 1.79-1.81 (3H, m), 1.88 (1H, dt, J=10.7, 7.5 Hz), 2.15-2.22 (1H, m), 2.39 (1H, dd, J=10.7, 7.5 Hz), 3.00-3.01 (2H, m), 3.96 (1H, dd, J=8.8, 11.1 Hz), 4.07 (1H, dd), J=6.5, 11.1 Hz), 4.56 (1H, s), 4.79-4.81 (1H, m), 4.83-4.84 (1H, m), 4.89-4.91 (1H, m) ppm.

$^{13}$C-NMR (150 MHz, CDCl$_3$): δ=16.09, 22.46, 22.86, 22.94, 30.91, 39.78, 41.07, 43.57, 48.81, 65.12, 109.44, 114.61, 138.52, 144.94, 171.32, ppm.

Example 24

Preparation of (3-isopropylidene-2,2-dimethylcyclobutyl)methyl 2-methylbutanoate

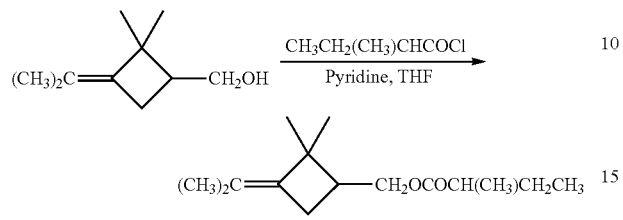

(3-Isopropylidene-2,2-dimethylcyclobutyl)methanol (9.16 g, 59.4 mmol) obtained according to Example 15, tetrahydrofuran (THF) (100 g), and pyridine (14.1 g) were placed in a reactor in a nitrogen atmosphere and stirred at 0° C. 2-Methylbutanoyl chloride (10.8 g, 89.2 mmol) was added dropwise at an internal temperature in the reactor of 15° C. or below. After the completion of the dropwise addition, the mixture was heated gradually up to 20° C. for 3 hours with stirring. Subsequently, brine was added to the reaction mixture, and the organic layer was separated and subjected to post-treatment by ordinary washing, drying and concentration. Then, the obtained concentrated liquid was subjected to distillation at a reduced pressure to obtain the target compound, (3-isopropylidene-2,2-dimethylcyclobutyl)methyl 2-methylbutanoate, (14.2 g, 59.4 mmol) in a yield of 100%.

The following is spectrum data of (3-isopropylidene-2,2-dimethylcyclobutyl)methyl 2-methylbutanoate (colorless or pale yellow oily liquid) thus produced.

IR (D-ATR): νmax 2964, 2935, 2878, 1735, 1461, 1383, 1361, 1264, 1240, 1186, 1152, 1081, 1013, 973, 889, 755 cm$^{-1}$.

$^1$H-NMR (500 MHz CDCl$_3$): δ 0.89 (3H, t, J=7.5 Hz), 1.13 (3H, d, J:=8.0 Hz), 1.13 (3H, s), 1.24 (3H, s), 1.42-1.50 (4H, m), 1.57 (3H, t, J=1.7 Hz). 1.60-1.77 (1H, m), 2.09-2.23 (2H, m), 2.30-2.39 (1H, m), 2.55-2.61 (1H, m), 4.08-4.15 (2H, m) ppm.

$^{13}$C-NMR (150 MHz, CDCl$_3$): δ=11.64, 16.58, 16.63, 18.50, 19.54, 21.02, 21.04, 26.72, 26.75, 27.50, 27.52, 28.40, 39.12, 39.15, 41.17, 44.20, 65.33, 122.60, 136.99, 176.73 ppm.

The invention claimed is:

1. A diester compound of general formula (1), having a dimethylcyclobutane ring,

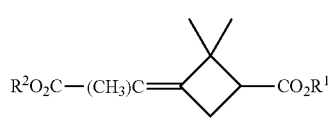

wherein R$^1$ and R$^2$ represent, independently of each other, a monovalent hydrocarbon group having 1 to 10 carbon atoms.

2. A process for preparing the diester compound of claim 1 of general formula (1), having a dimethylcyclobutane ring,

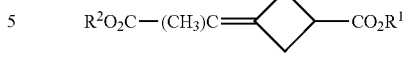

wherein R$^1$ and R$^2$ represent, independently of each other, a monovalent hydrocarbon group having 1 to 10 carbon atoms,
the process comprising
reacting a dimethylcyclobutanone compound of general formula (2):

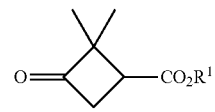

wherein R$^1$ is as defined above,
with a phosphonic ester compound of general formula (3):

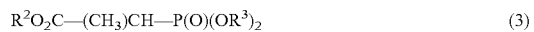

wherein R$^2$ is as defined above, and R$^3$ represents a monovalent hydrocarbon group having 1 to 10 carbon atoms,
to produce the diester compound (1), having a dimethylcyclobutane ring.

3. A process for preparing a diol compound of formula (4), having a dimethylcyclobutane ring,

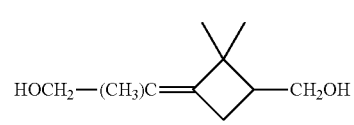

the process comprising
subjecting the diester compound of claim 2 of general formula (1), having a dimethylcyclobutane ring,

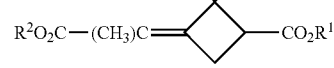

wherein R$^1$ and R$^2$ represent, independently of each other, a monovalent hydrocarbon group having 1 to 10 carbon atoms,
to a reduction reaction to produce the diol compound (4), having a dimethylcyclobutane ring.

4. The diester compound of claim 3 of general formula (1), wherein the diester compound has a chemical structure selected from the following:

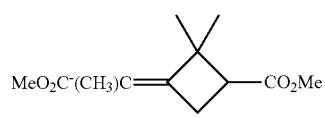

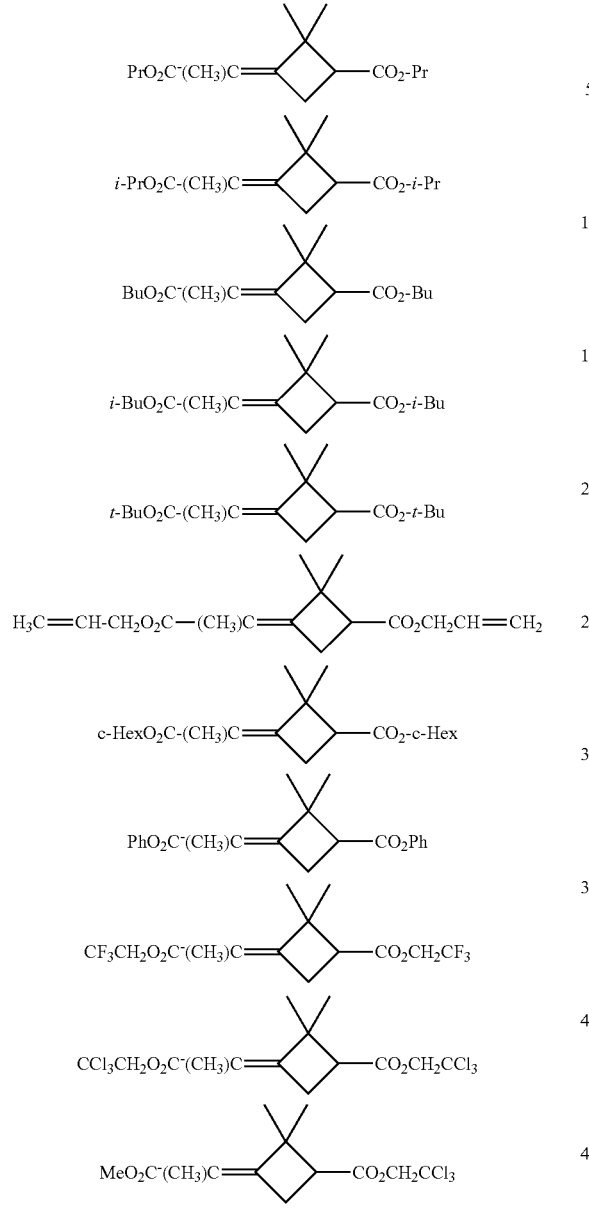
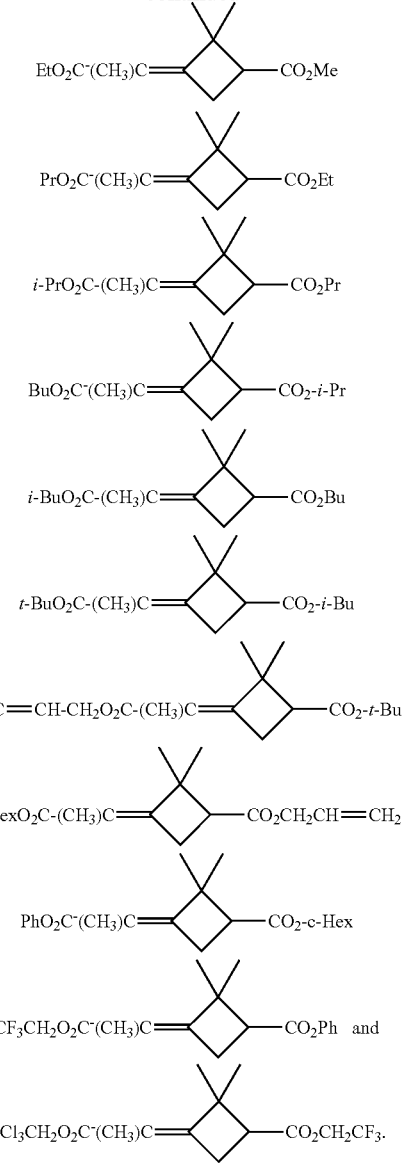

UNITED STATES PATENT AND TRADEMARK OFFICE
CERTIFICATE OF CORRECTION

PATENT NO. : 11,352,312 B2
APPLICATION NO. : 16/930578
DATED : June 7, 2022
INVENTOR(S) : Ishibashi et al.

It is certified that error appears in the above-identified patent and that said Letters Patent is hereby corrected as shown below:

In the Specification

Column 7, Lines 45-50: Please remove the compound and replace with the following:

Column 7, Lines 53-57: Please remove the compound and replace with the following:

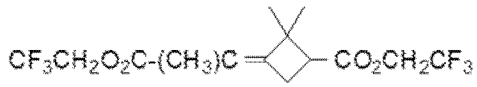

Column 8, Lines 17-21: Please remove the compound and replace with the following:

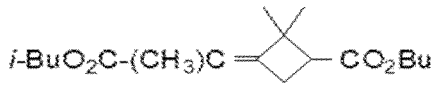

Column 8, Lines 30-33: Please remove the compound and replace with the following:

Column 8, Lines 34-37: Please remove the compound and replace with the following:

Column 17, Line 52: Please correct "(LC)" to read --(TLC)--

Column 19, Line 25: Please correct "$X^1$" to read --$X^6$--

Column 20, Line 9: Please correct "(A)" to read --(5A)--

Signed and Sealed this
Third Day of October, 2023

Katherine Kelly Vidal
*Director of the United States Patent and Trademark Office*

Column 26, Line 9: Please correct "$X^3$" to read --$X^5$--

Column 27, Line 55: Please correct "(713)" to read --(7B)--

Column 30, Line 62: Please correct "(6))" to read --(6D)--

Column 30, Line 63: Please correct "(71)" to read --(7D)--

Column 32, Line 4: Please correct "(71)" to read --(7D)--

Column 33, Line 29: Please correct "(71))" to read --(7D)--

Column 33, Line 59: Please correct "NAH, THF" to read --NaH, THF--

Column 35, Line 24: Please correct "δ 14.19" to read --δ=14.19--

Column 35, Line 34: Please correct "J 1.3 Hz" to read --J=1.3Hz--

Column 36, Line 25: Please correct "J 5.4 Hz" to read --J=5.4 Hz--

Column 38, Line 18: Please correct "(3H, a)" to read --(3H, s)--

Column 38, Line 21: Please correct "J 14.6 Hz" to read --J=14.6 Hz--

Column 38, Line 67: Please correct "J 9.6 Hz" to read --J=9.6 Hz--

Column 39, Line 54: Please correct "oily 16 liquid" to read --oily liquid--

Column 42, Line 43: Please correct "21.7 nmol" to read --21.7 mmol--

Column 42, Line 50: Please correct "acetate 80:1" to read --acetate=80:1--

Column 43, Line 28: Please correct "19.1 nmol" to read --19.1 mmol--

Column 46, Line 64: Please correct "acetate 50:1" to read --acetate=50:1--

Column 47, Line 46: Please correct "J 1.9 Hz" to read --J=1.9 Hz--

Column 49, Line 42: Please correct "(TH)" to read --(THF)--

Column 49, Line 52: Please correct "layer 16 was" to read --layer was--

Column 50, Line 48: Please correct "85.6 nmol" to read --85.6 mmol--

Column 50, Line 56: Please correct "cm-1." to read --$cm^{-1}$.--

CERTIFICATE OF CORRECTION (continued)
U.S. Pat. No. 11,352,312 B2

Column 50, Line 59: Please correct "J 10.7 Hz" to read --J=10.7 Hz--

Column 51, Line 41: Please correct "δ 0.89" to read --δ=0.89--

Column 51, Line 42: Please correct "J:=8.0 Hz" to read --J=8.0 Hz--

In the Claims

Column 52, Line 43, Claim 3: Please correct "claim 2" to read --claim 1--

Column 52, Line 58, Claim 4: Please correct "claim 3" to read --claim 1--

Column 53, Line 25, Claim 4: Please correct "H₃C" to read --H₂C--

Column 53, Lines 22-26, Claim 4: Please remove the compound and replace with the following: